(12) United States Patent
Bettati et al.

(10) Patent No.: US 7,728,022 B2
(45) Date of Patent: Jun. 1, 2010

(54) (4, 5, 6, 7-TETRAHYDRO-1-H-INDOL-7-YL) ACETIC ACID DERIVATIVES FOR TREATMENT OF ALZHEIMER'S DISEASE

(75) Inventors: Michela Bettati, Sawbridgeworth (GB); Ian Churcher, Royston (GB); Victoria Alexandra Doughty, Stansted (GB); Timothy Harrison, Great Dunmow (GB); Emmanuela Nizi, Siena (IT); Adam Smith, Bishops Stortford (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 668 days.

(21) Appl. No.: 11/587,779

(22) PCT Filed: May 6, 2005

(86) PCT No.: PCT/GB2005/001756

§ 371 (c)(1), (2), (4) Date: May 22, 2007

(87) PCT Pub. No.: WO2005/108362

PCT Pub. Date: Nov. 17, 2005

(65) Prior Publication Data

US 2007/0232678 A1 Oct. 4, 2007

(30) Foreign Application Priority Data

May 7, 2004 (GB) .................................. 0410238.0

(51) Int. Cl.
*A61K 31/41* (2006.01)
*A61K 31/403* (2006.01)
*C07D 403/06* (2006.01)
*C07D 209/12* (2006.01)

(52) U.S. Cl. ........................ 514/381; 514/412; 548/250; 548/516

(58) Field of Classification Search ........................ None
See application file for complete search history.

(56) References Cited

FOREIGN PATENT DOCUMENTS

| BE | 806 805 | 2/1974 |
|---|---|---|
| EP | 1 193 260 | 4/2002 |
| WO | WO 99/25340 | 5/1999 |
| WO | WO 01/78721 | 10/2001 |
| WO | WO 02/48150 | 6/2002 |
| WO | WO 2004/064771 | 8/2004 |
| WO | WO 2005/013985 | * 2/2005 |

* cited by examiner

*Primary Examiner*—Golam M. M. Shameem
*Assistant Examiner*—Alicia L Fierro
(74) *Attorney, Agent, or Firm*—Gerard Devlin; Raynard Yuro

(57) ABSTRACT

Compounds of formula I:

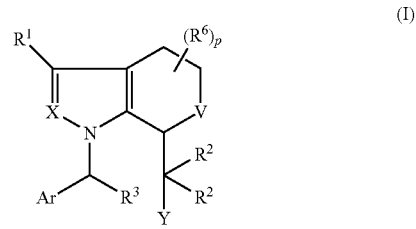

are disclosed. The compounds are useful in treating or preventing diseases associated with deposition of Aβ in the brain.

11 Claims, No Drawings

(4, 5, 6, 7-TETRAHYDRO-1-H-INDOL-7-YL) ACETIC ACID DERIVATIVES FOR TREATMENT OF ALZHEIMER'S DISEASE

CROSS REFERENCE TO RELATED APPLICATIONS

This application is a U.S. National Phase application under 35 U.S.C. §371 of PCT Application No. PCT/GB2005/001756, filed May 6, 2005, which claims priority under 35 U.S.C. §119(a) from Great Britain provisional application no. 0410238.0, filed May 7, 2004.

This invention relates to methods and materials for use in therapeutic treatment of the human body. In particular, it provides materials for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, PNAS, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, Science, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, Nature, 423 (2003), 435-9).

Other proposed methods of treatment include administering a compound which blocks the aggregation of Aβ, and administering an antibody which selectively binds to Aβ.

An alternative method of treatment is that of modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al Nature, 414 (2001) 212-16; Morihara et al, J. Neurochem., 83 (2002), 1009-12; and Takahashi et al, J. Biol. Chem., 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, J. Neuroscience, 22 (2002), 226-54).

It has now been found that certain tetrahydroindole alkanoic acids and related compounds have the desirable property of selectively inhibiting production of Aβ(1-42).

According to the present invention there is provided a compound of formula I:

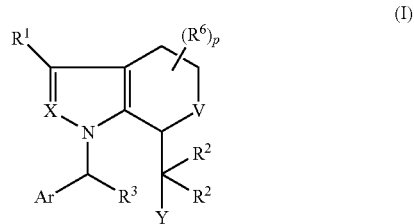

wherein V represents a bond, $CH_2$ or $CH_2CH_2$;

X represents $CR^{1a}$ or N;

Y represents $CO_2H$ or tetrazole;

Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$, $OR^4$, $S(O)_tR^4$ where t is 0, 1 or 2, $CO_2R^4$, tetrazole, $N(R^4)_2$, $NHCOR^5$, $NHCON(R^4)_2$, $CON(R^4)_2$, $SO_2N(R^4)_2$, $NHSO_2R^5$, $COR^5$, or $OCOR^5$;

$R^1$ represents H or a nonaromatic hydrocarbon group of up to 10 carbon atoms optionally substituted with up to 3 halogen substituents or with CN, $CF_3$, $OR^4$, $S(O)_tR^4$ where t is 0, 1 or 2, $CO_2R^4$, $CON(R^4)_2$, $SO_2N(R^4)_2$, $COR^4$, $OCOR^5$ or $NR^4COR^5$;

or $R^1$ represents phenyl, naphthyl, benzyl or heteroaryl any of which optionally bears up to 3 substituents selected from halogen, $CF_3$, $OCF_3$, CN, $NO_2R^5$, $OR^4$, $CO_2R^4$, $S(O)_tR^4$ where t is 0, 1 or 2, $CON(R^4)_2$, $SO_2N(R^4)_2$, $COR^4$, $OCOR^5$ or $NR^4COR^5$;

$R^{1a}$ has the same definition as $R^1$;

each $R^2$ is independently H or $C_{1-4}$alkyl;

$R^3$ is H or a hydrocarbon group containing up to 10 carbon atoms which is optionally substituted with halogen, $CF_3$, $C_{1-4}$alkoxy or $C_{1-4}$alkylthio;

$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl; or two $R^4$ groups attached to the same nitrogen atom may complete a 5- or 6-membered heterocyclic ring;

$R^5$ represents $R^4$ that is other than H;

p is 0, 1 or 2; and $R^6$ represents $C_{1-6}$alkyl, $C_{2-6}$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;

or a pharmaceutically acceptable salt thereof.

In a particular embodiment, $R^1$ represents H or a nonaromatic hydrocarbon group of up to 10 carbon atoms optionally substituted with up to 3 halogen substituents or with CN, $CF_3$, $OR^4$, $S(O)_tR^4$ where t is 0, 1 or 2, $CO_2R^4$, $CON(R^4)_2$, $SO_2N(R^4)_2$, $COR^4$, $OCOR^5$ or $NR^4COR^5$;

or $R^1$ represents phenyl, benzyl or heteroaryl any of which optionally bears up to 3 substituents selected from halogen, $CF_3$, $OCF_3$, CN, $R^5$, $OR^4$, $CO_2R^4$, $S(O)_tR^4$ where t is 0, 1 or 2, $CON(R^4)_2$, $SO_2N(R^4)_2$, $COR^4$, $OCOR^5$ or $NR^4COR^5$;

$R^{1a}$ has the same definition as $R^1$ with the proviso that when X is $CR^{1a}$, at least one of $R^1$ and $R^{1a}$ is H or $C_{1-4}$ alkyl;

and all other variables are as defined above.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine, of which fluorine and chlorine are preferred.

The term "heteroaryl" as used herein means a cyclic or polycyclic system of up to 10 ring atoms selected from C, N, O and S, wherein at least one of the constituent rings is aromatic and wherein at least one atom of the aromatic ring is other than carbon. Preferably not more than 3 ring atoms are other than carbon. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine, 1,3,5-triazine, 1,2,3,4-tetrahydroquinoline and 1,2,3,4-tetrahydroisoquinoline. Monocyclic 5- or 6-membered systems are preferred, especially pyridine or thiophene.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula I, V represents a bond, $CH_2$ or $CH_2CH_2$. In a preferred embodiment V represents $CH_2$.

X represents N or $CR^{1a}$, preferably $CR^{1a}$.

$R^3$ represents H or a hydrocarbon group of up to 10 carbon atoms which is optionally substituted as defined previously. Suitable identities for $R^3$ include H; alkyl (especially $C_{1-6}$alkyl such as methyl, ethyl, n-propyl, isopropyl, 2-methylpropyl, n-butyl, 3-methylbutyl and 3,3-dimethylbutyl); substituted alkyl (such as methoxymethyl, methylthiomethyl and 3,3,3-trifluoropropyl); cycloalkyl (especially $C_{3-6}$cycloalkyl such as cyclopropyl, cyclopentyl and cyclohexyl); cycloalkylalkyl (such as cyclopropylmethyl); aryl (such as phenyl and 4-trifluoromethylphenyl) and arylalkyl (such as benzyl and phenethyl). In a particular embodiment, $R^3$ is an optionally-substituted hydrocarbon group of 2 to 10 carbon atoms, preferably 2 to 6 carbon atoms, and in particular an alkyl group of 2 to 6 carbon atoms. In a preferred embodiment, $R^3$ is n-propyl, n-butyl or 3-methylbutyl.

Y represents $CO_2H$ or tetrazole (in particular 1,2,3,4-tetrazol-5-yl), but preferably represents $CO_2H$.

Ar represents phenyl which is optionally substituted as defined previously. Phenyl groups represented by Ar optionally bear up to 3 substituents as defined previously. When said substituents comprise a group represented by $(CH_2)_m$—Z, m is preferably 0 or 1, most preferably 0. When Ar represents mono-substituted phenyl, the substituent aptly occupies the 4-position. Examples of suitable substituents include halogen (especially Cl and F), $N_3$, $CF_3$, $OCF_3$, OH, OMe, SMe, NHCOMe, $SO_2Me$, $CO_2H$, $CO_2Me$, $C_{1-4}$alkyl (such as methyl, ethyl, n-propyl and isopropyl), $CON(Me)_2$, COMe, $SO_2N(Me)_2$, $NHSO_2Me$ and NHCONHMe. Preferred substituents include Cl, F, $N_3$, $OCF_3$, $CF_3$ and OMe.

Specific examples of groups represented by Ar include phenyl, 4-chlorophenyl, 4-trifluoromethylphenyl, 4-fluorophenyl, 4-azidophenyl, 4-methoxyphenyl, 4-trifluoromethoxyphenyl, 2,4-bis(trifluoromethyl)phenyl, 3,4-dichlorophenyl, 2,4-dichlorophenyl, 2,4,6-trifluorophenyl and 4-iodophenyl, of which 4-trifluoromethylphenyl is particularly preferred.

$R^1$ preferably represents H or a hydrocarbon group of up to 6 carbon atoms, or phenyl, naphthyl, benzyl or heteroaryl, any of which may be substituted as defined previously. Very suitably, $R^1$ represents optionally-substituted phenyl or heteroaryl (such as thiophene). Preferred substituents include halogen (especially Cl, Br or F), $C_{1-6}$ alkyl (such as methyl, ethyl, n-propyl, isopropyl, n-butyl, t-butyl and 2-methylpropyl), $OCF_3$, methoxy and $CF_3$. Specific examples of groups represented by $R^1$ include H, phenyl, 4-methylphenyl, 4-isopropylphenyl, 2-chlorophenyl, 2-bromophenyl, 2-trifluoromethylphenyl, 2,4-dichlorophenyl, 2,5-dichlorophenyl, 2,6-dichlorophenyl, 2,3-dichlorophenyl, 3,4-dichlorophenyl, 3,5-dichlorophenyl, 4-chlorophenyl, 3-trifluoromethylphenyl, 2-bromo-4-chlorophenyl, 2-n-butyl-4-chlorophenyl, 4-chloro-2-(2-methylpropyl)phenyl and 5-chloro-2-thienyl.

Further specific examples of groups represented by $R^1$ include 4-chloro-2-methylphenyl, 2,4-dimethylphenyl, 4-cyanophenyl, 2,4-bis(trifluoromethyl)phenyl, 4-trifluoromethylphenyl, 2,4-dimethoxyphenyl, 4-t-butylphenyl, 2,5-dimethylphenyl, 4-methyl-1-naphthyl, 2-nitrophenyl, 4-trifluoromethoxyphenyl, 5-chlorobiphenyl-2-yl, 2,4,6-trichlorophenyl, 2,5-bis(trifluoromethyl)phenyl, 2,4-difluorophenyl, 4-chloro-2-fluorophenyl and t-butyl.

$R^{1a}$ has the same definition as $R^1$, i.e. is selected from the same range of chemical structures, but is preferably not identical to $R^1$. Preferred identities for $R^{1a}$ include H, $C_{1-6}$alkyl (such as methyl, ethyl, isopropyl and t-butyl), $C_{3-7}$cycloalkyl (such as cyclohexyl) and phenyl which is optionally-substituted as described for $R^1$ (in particular 4-trifluoromethylphenyl and 2,4-dichlorophenyl). In one embodiment, when X is $CR^{1a}$ at least one of $R^1$ and $R^{1a}$ is H or $C_{1-4}$ alkyl. In another embodiment, $R^1$ represents optionally-substituted phenyl, naphthyl or heteroaryl and $R^{1a}$ represents H, $C_{1-6}$alkyl or $C_{3-7}$cycloalkyl, preferably H or $C_{1-4}$alkyl.

In a further embodiment, $R^1$ represents H and $R^{1a}$ represents $C_{1-6}$alkyl, $C_{3-7}$cycloalkyl or optionally-substituted phenyl.

Each $R^2$ is independently H or $C_{1-4}$alkyl such as methyl or ethyl. Preferably one $R^2$ is H and the other is H or methyl. Most preferably, both $R^2$ groups are H.

When present, $R^6$ represents linear or branched $C_{1-6}$alkyl (preferably $C_{1-4}$alkyl) such as methyl, ethyl, n-propyl, isopropyl or t-butyl, $C_{2-6}$ alkenyl such as vinyl or allyl, or phenyl, heteroaryl or benzyl which is optionally substituted as defined previously. Preferred substituents include halogen (especially Cl or F), $OCH_3$, $OCF_3$, $CF_3$ and $C_{1-4}$alkyl (such as methyl). A preferred heteroaryl group is pyridyl, especially 3-pyridyl. Examples of groups represented by $R^6$ include methyl, ethyl, isopropyl, vinyl, 3-pyridyl, phenyl, 4-chlorophenyl, 3-fluorophenyl, 4-fluorophenyl, 4-fluoro-3-methylphenyl, 4-methoxyphenyl, 3,4-dichlorophenyl, 3,4-difluorophenyl and 2,5-dimethylphenyl. Preferred examples include 4-fluorophenyl. An $R^6$ group may be attached at any available position of the ring, including the carbon atom bearing the $-C(R^2)_2-Y$ moiety and any carbon atom included in V. Where two $R^6$ groups are present, they may be the same or different and may be attached to the same or different ring positions. When p is 2, preferably not more than one of the $R^6$ groups is optionally-substituted phenyl, heteroaryl or benzyl.

A subset of the compounds of Formula I is defined by Formula II:

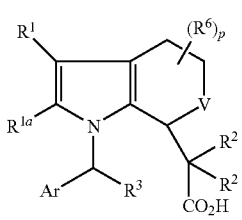

II wherein V, Ar, p, $R^1$, $R^{1a}$, $R^2$, $R^3$ and $R^6$ have the same definitions and preferred identities as before.

A subset of the compounds in accordance with formula II comprises the 1-arylalkyl-4,5,6,7-tetrahydroindol-7-yl acetic acid derivatives in which V is $CH_2$ and each $R^2$ is H. Within this embodiment, p is preferably 0 or p is 1 and $R^6$ is attached in the 4-position or the 6-position. Ar is very suitably 4-trifluoromethylphenyl, $R^1$ is very suitably selected from the examples listed earlier herein, $R^{1a}$ is very suitably selected from H or $C_{1-4}$alkyl, and $R^3$ is very suitably n-propyl, n-butyl or 3-methylbutyl.

A second subset of the compounds of formula I is defined by formula III:

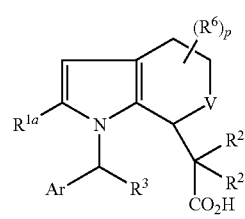

III wherein V, Ar, p, $R^{1a}$, $R^2$, $R^3$ and $R^6$ have the same definitions and preferred identities as before. Preferred compound within this subset include those in which V represents $CH_2$ and either p is 0 or p is 1 and $R^6$ represents an alkyl substituent in the 6-position, especially ethyl. In formula III, Ar preferably represents 4-trifluoromethylphenyl, each $R^2$ is preferably H, $R^3$ is preferably n-propyl, n-butyl or 3-methylbutyl, and $R^{1a}$ is preferably selected from $C_{1-6}$alkyl (especially methyl, ethyl, isopropyl or t-butyl), $C_{3-7}$ cycloalkyl (especially cyclohexyl), or optionally-substituted phenyl (especially 4-trifluoromethylphenyl or 2,4-dichlorophenyl).

A third subset of the compounds of formula I is defined by formula IV:

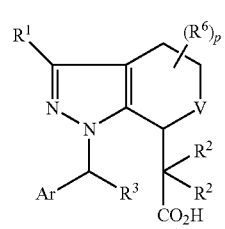

IV where V, p, Ar, $R^1$, $R^2$, $R^3$ and $R^6$ have the same definitions and preferred identities as before.

Specific examples of compounds in accordance with formula I are provided in the Examples appended hereto.

Compounds of formula I in which X represents CH may be obtained by reaction of an imine (1) with a nitro-olefin (2):

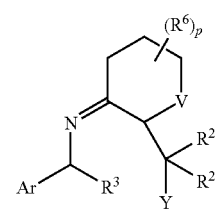

(1)

-continued

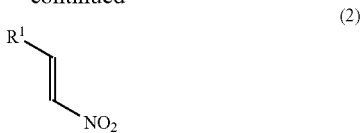
(2)

wherein V, Ar, Y, p, $R^2$, $R^3$, $R^6$ and $R^1$ have the same meanings as before. Preferably $R^1$ is optionally substituted phenyl or heteroaryl. The reaction takes place in toluene solution, eg at reflux or by heating in a microwave apparatus.

Imines of formula (1) are conveniently generated in situ by reaction of an amine (3) with a cyclohexanone of formula (4):

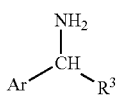
(3)

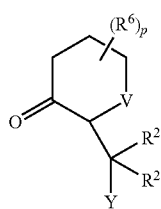
(4)

where V, Ar, $R^3$, Y, p, $R^2$ and $R^6$ have the same meanings as before. The reaction can be carried out in toluene with azeotropic removal of water.

Amines (3) may be obtained by treating ketones Ar—CO—$R^3$ with hydroxylamine and hydrogenating the resulting oximes over Raney nickel. Alternatively, ketones Ar—CO—$R^3$ may be condensed with α-methylbenzylamine and the resulting imines reduced (using $NaBH_4$) to provide bis(benzylamines) ArCH($R^3$)—NH—CH($CH_3$)Ph, from which the desired amines (3) are obtained by hydrogenation over Pd/C. Use of a chiral α-methylbenzylamine facilitates isolation of amines (3) as single enantiomers, enabling control of the stereochemistry at one of the chiral centres in formula I.

Compounds of formula I in which X represents $CR^{1a}$ may be obtained by reaction of an amine (3) with a 1,4-dicarbonyl compound (5):

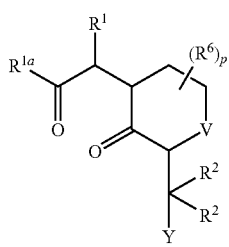
(5)

The reaction takes place in toluene solution in the presence of an acid catalyst (eg. acetic acid) with azeotropic removal of water. Alternatively, the reaction can be carried out in dichloromethane at −78° C. in the presence of triethylamine and $TiCl_4$.

Compounds (5) are available by reaction of an enamine (6):

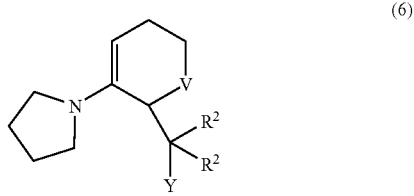
(6)

with a halo-ketone $R^{1a}$—CO—CH($R^1$)-Hal where Hal is chloride or bromide. The reaction takes place in DMF at ambient temperature and is particularly suitable when $R^1$ is H or alkyl.

Enamines (6) are formed from ketones (4) by refluxing with pyrrolidine in toluene solution using an acid catalyst such as acetic acid with azeotropic removal of water.

A preferred route to dicarbonyl compounds (5) comprises oxidative cleavage of olefins (7):

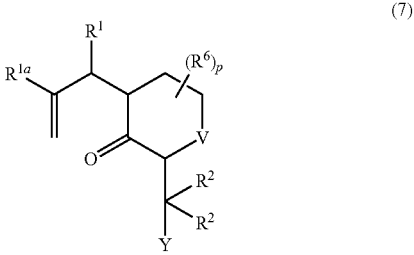
(7)

where V, Y, p, $R^1$, $R^{1a}$, $R^2$ and $R^6$ have the same meanings as before. The cleavage may be effected by ozonolysis in methanol/dichloromethane, or alternatively by treatment with $RuCl_3$ and $NaIO_4$. Ozonolysis is preferred when $R^{1a}$ is H.

Olefins (7) may be obtained by treatment of ketones (4) with triethylorthoformate, and reaction of the resulting diethyl ketals with an allylic alcohol (8):

(8)

where $R^1$ and $R^{1a}$ have the same meanings as before. The reaction may be carried out at about 125° C. in the presence of propionic acid. The initial product is an enol ether which undergoes Claisen rearrangement to provide the olefin (7).

In an alternative route to compounds of formula I in which X represents C—$CH_3$ and $R^1$ is H, alkynes (9):

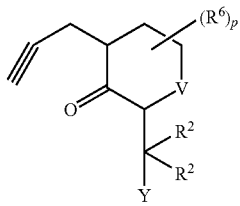

may be substituted for diketones (5). Alkynes (9) are formed by reaction of enamines (6) with propargyl bromide in toluene at 80° C.

Compounds of formula I in which X is N may be obtained by reaction of diketones (10) with hydrazines (11):

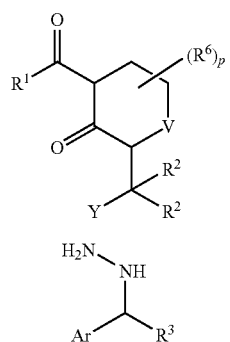

The reaction takes place in refluxing ethanol. Diketones (10) are available by reaction of enamines (6) with $R^1$—COCl. Hydrazines (11) are available by reaction of Ar—CH($R^3$)—Br with hydrazine hydrate in isopropanol at 70° C. (see also EP 0234708).

During all of the chemical processes described above, a carboxylic acid group represented by Y is preferably protected as the methyl ester or ethyl ester, the free acid being regenerated by hydrolysis in a final step, e.g. using LiOH in aqueous THF or dioxan.

Where they are not commercially available, the starting materials used in the schemes outlined above may be obtained by published routes or simple adaptations thereof. Suitable methods are described in the Examples section herein.

Since the compounds of Formula I have at least one asymmetric centre, they accordingly exist in enantiomeric forms. If desired, the individual enantiomers may be isolated in pure form by conventional means. For example, a racemic mixture may be resolved into its component enantiomers by preparative chiral HPLC, or by treatment with an optically pure amine to form diastereomeric salt pairs, separable by fractional crystallisation, from which the optically pure acids may be regenerated. Similarly, a racemic acid may be reacted with an optically pure alcohol or amine to form pairs of diastereomeric esters or amides which may be separated by chromatography or fractional crystallisation and hydrolysed to yield enantiomerically-pure acids. These resolution techniques may equally well be practised on the synthetic precursors of the compounds of Formula I, and the resulting optically-pure intermediates used to prepare compounds of Formula I in optically-pure form.

The invention further provides a pharmaceutical composition comprising compound of formula I or pharmaceutically acceptable salt thereof and a pharmaceutically acceptable carrier.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The invention also provides a compound of formula I or a pharmaceutically acceptable salt thereof for use in therapy, in particular for use in treatment or prevention of a disease associated with deposition of Aβ in the brain.

The invention further provides the use of a compound of formula I or a pharmaceutically acceptable salt thereof for the manufacture of a medicament for treatment or prevention of a disease associated with deposition of Aβ in the brain.

The disease associated with deposition of Aβ in the brain is typically Alzheimer's disease (AD), cerebral amyloid angiopathy, multi-infarct dementia, dementia pugilistica or Down syndrome, preferably AD.

In another aspect, the invention provides the use of a compound of Formula I as defined above, or a pharmaceutically acceptable salt thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are also controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound.

The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ.

In this embodiment of the invention, the amyloid modifier may be a compound which inhibits the secretion of Aβ, for example an inhibitor of γ-secretase (such as those disclosed in WO 01/53255, WO 01/66564, WO 01/70677, WO 01/90084, WO 01/77144, WO 02/30912, WO 02/36555, WO 02/081435, WO 02/081433, WO 03/018543, WO 03/013506, WO 03/013527 and WO 03/014075), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature*, 423 (2003), 435-9.

Within this embodiment, the amyloid modifier is advantageously a γ-secretase inhibitor, preferred examples of which include a compound of formula XI:

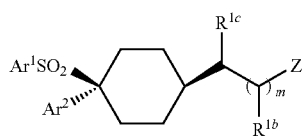

XI wherein:
m is 0 or 1;
Z represents halogen, CN, $NO_2$, $N_3$, $CF_3$, $OR^{2a}$, $N(R^{2a})_2$, $CO_2R^{2a}$, $OCOR^{2a}$, $COR^{2a}$, $CON(R^{2a})_2$, $OCON(R^{2a})_2$, $CONR^{2a}(OR^{2a})$, $CON(R^{2a})N(R^{2a})_2$ $CONHC(=NOH)R^{2a}$, heterocyclyl, phenyl or heteroaryl, said heterocyclyl, phenyl or heteroaryl bearing 0-3 substituents selected from halogen, CN, $NO_2$, $CF_3$, $OR^{2a}$, $N(R^{2a})_2$, $CO_2R^{2a}$, $COR^{2a}$, $CON(R^{2a})_2$ and $C_{1-4}$alkyl;
$R^{1b}$ represents H, $C_{1-4}$alkyl or OH;
$R^{1c}$ represents H or $C_{1-4}$alkyl;
with the proviso that when m is 1, $R^{1b}$ and $R^{1c}$ do not both represent $C_{1-4}$alkyl;
$Ar^1$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$R^{2a}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, $OR^{2b}$, $CO_2R^{2b}$, $N(R^{2b})_2$, $CON(R^{2b})_2$, Ar and COAr; or $R^{2a}$ represents Ar; or two $R^{2a}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

$R^{2b}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr; or $R^{2b}$ represents Ar; or two $R^{2b}$ groups together with a nitrogen atom to which they are mutually attached may complete an N-heterocyclyl group bearing 0-4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

Such compounds may be prepared as described in WO 03/018543. Preferred examples include those defined by formula XIa:

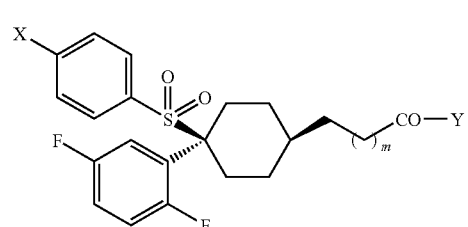

XI(a)

and the pharmaceutically acceptable salts thereof, wherein m is 0 or 1, X is Cl or $CF_3$, and Y is OH, $OC_{1-6}$alkyl, $NH_2$ or $NHC_{1-6}$alkyl. Particular examples include those in which m is 1 and Y is OH (or the sodium salts thereof), and those in which m is 0 and Y is $NH_2$ or $NHC_{1-6}$alkyl.

Another preferred class of γ-secretase inhibitors for use in this embodiment of the invention is that defined by formula XII:

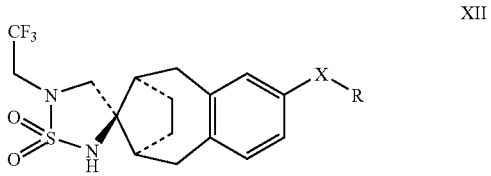

wherein X is a bivalent pyrazole, imidazole, triazole, oxazole, isoxazole, thiazole, isothiazole, thiadiazole or 1,3,4-oxadiazole residue optionally bearing a hydrocarbon substituent comprising 1-5 carbon atoms which is optionally substituted with up to 3 halogen atoms; and R is selected from:

(i) $CF_3$ or a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl;

(ii) a non-aromatic heterocyclic group comprising up to 7 ring atoms of which up to 3 are chosen from N, O and S and the remainder are carbon, bearing 0-3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl;

(iii) phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy; and (iv) $N(R^a)_2$ where each $R^a$ independently represents H or $C_{1-6}$alkyl which is optionally substituted with halogen, $CF_3$, $CHF_2$, CN, OH, $CO_2H$, $C_{2-6}$acyl, $C_{1-4}$alkoxy or $C_{1-4}$alkoxycarbonyl;

or a pharmaceutically acceptable salt thereof.

X is very aptly 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl. Preferably, R represents optionally-substituted phenyl or heteroaryl such as phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Particularly preferred identities of R—X— include 5-(4-fluorophenyl)-1-methylpyrazol-3-yl, 5-(4-chlorophenyl)-1-methylpyrazol-3-yl and 1-(4-fluorophenyl)imidazol-4-yl. Such compounds may be prepared by methods disclosed in WO 03/093252.

Alternatively, the amyloid modifier may be a compound which inhibits the aggregation of Aβ. Suitable examples include chelating agents such as clioquinol (Gouras and Beal, Neuron, 30 (2001), 641-2) and the compounds disclosed in WO 99/16741, in particular that known as DP-109 (Kalendarev et al, J. Pharm. Biomed. Anal., 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 and the compound known as Alzhemed™ (Neurochem); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

In a further aspect, the invention provides the combination of a compound of formula I or a pharmaceutically acceptable salt thereof and a compound of formula XI(a) or a pharmaceutically acceptable salt thereof for use in treatment or prevention of a disease associated with deposition of β-amyloid in the brain. Said use may involve the simultaneous or separate administration of the respective compounds to a patient in need of such treatment or prevention.

In a further aspect, the invention provides a pharmaceutical composition comprising, in a pharmaceutically acceptable carrier, a compound of formula I or a pharmaceutically acceptable salt thereof and a compound of formula XI(a) or a pharmaceutically acceptable salt thereof. Preferably, the pharmaceutical composition is in a unit dose form suitable for oral administration, such as a tablet or a capsule.

The ability of the compounds of Formula I to selectively inhibit production of Aβ(1-42) was determined using the following assay:

Cell-based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% CO$_2$, 10 μl and 50 μl media were transferred into a fresh Costar round-bottom 96-well plate for detection of Aβ(40) and Aβ(42) peptides, respectively. 40 μl Origen buffer (PBS, 2% BSA, 0.2% Tween-20) was added to the Aβ(40) wells followed by the addition of 25 μl the respective antibody premixes to the wells:

Aβ(40) premix: 1 μg/ml ruthenylated G2-10 antibody, 4 μg/ml biotinylated 4G8 antibody diluted in Origen buffer Aβ(42) premix: 0.5 μg/ml ruthenylated G2-11 antibody, 4 μg/ml biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Origen M8 Analyser (Igen Inc.) was calibrated according to the manufacturer's instructions. 25 μl of streptavidin magnetic bead (Dynal) premix (400 μg/ml streptavidin beads/ml in Origen buffer) was added to the assay plates and incubated on a shaker for 15 minutes. 150 μl Origen buffer was added to each well and the plates were read on the Origen M8 Analyser according to the manufacturer's instructions.

Cell viability was measured in the corresponding cells after removal of the media for the Aβ assays by a calorimetric cell proliferation assay (CellTiter 96™ AQ assay, Promega) utilizing the bioreduction of MTS (Owen's reagent) to formazan according to the manufacturer's instructions. Briefly, 5 μl of 10× MTS/PES was added to the remaining 50 μl of media before returning to the incubator. The optical density was read at 495 nm after ~4 hours.

LD$_{50}$ and IC$_{50}$ values for inhibition of Aβ(40) and Aβ(42) were calculated by nonlinear regression fit analysis using the appropriate software (eg. Excel fit). The total signal and the background were defined by the corresponding Me$_2$SO and inhibitor controls.

The compounds of the invention give IC$_{50}$ values for Aβ(1-42) inhibition that are at least 2-fold lower than the corresponding IC$_{50}$ values for Aβ(1-40) inhibition, typically at least 5-fold lower, and in the preferred cases at least 50-fold lower.

EXAMPLES

Intermediate 1

(R/S)-1-[4-(trifluoromethyl)phenyl]butan-1-amine

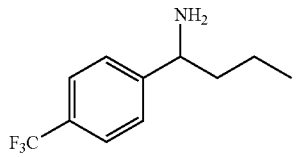

To a solution of 1-[4-(trifluoromethyl)phenyl]butan-1-one (6 g, 27.8 mmol) in ethanol (60 ml) was added hydroxylamine hydrochloride (5.79 g, 83.3 mmol) and the reaction heated to reflux and stirred for 16 h. The reaction was allowed to cool to room temperature and then concentrated in vacuo. The residue was taken up in ethyl acetate, washed twice with water, dried over sodium sulfate and concentrated in vacuo. The crude oxime was then dissolved in ethanol (100 ml) and Raney nickel (approx 1 g) added. The reaction was stirred under a balloon of hydrogen for 72 h. The reaction was filtered though celite (washing with ethanol) concentrated in vacuo, adsorbed onto silica gel and purified by flash column (50-80% ethyl acetate in hexanes) to yield the title compound (5 g, 83%) as colourless crystals.

$^1$H NMR δ (ppm)(CDCl$_3$): 7.58 (2 H, d, J=8.1 Hz), 7.43 (2 H, d, J=8.1 Hz), 3.97 (1 H, t, J=6.9 Hz), 1.68-1.60 (2 H, m), 1.50 (2 H, s), 1.36-1.21 (2 H, m), 0.91 (3 H, t, J=7.3 Hz).

Intermediate 2

Ethyl (2-pyrrolidin-1-ylcyclohex-2-en-1-yl)acetate

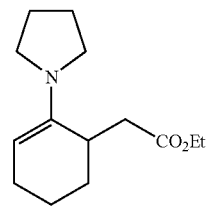

Ethyl 2-cyclohexanone acetate (1 g, 5.43 mmol) was dissolved in toluene (20 ml) and pyrrolidine (0.90 ml, 10.8 mmol, 2 eq.) and acetic acid (0.4 ml) added. Dean Stark apparatus was fitted to the flask and the reaction mixture was refluxed for 16 h. The reaction mixture was concentrated in vacuo to give a yellow oil (1.4 g). $^1$H NMR showed >90% conversion to the title compound.

Intermediate 3

3-Phenyl-1-[4-(trifluoromethyl)phenyl]propan-1-amine

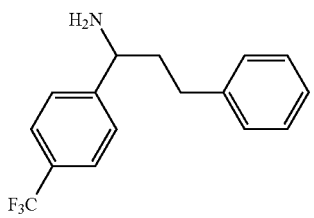

Hydroxylamine hydrochloride (2.1 g, 0.03 mol) was added to a solution of 3-phenyl-1-[4-(trifluoromethyl)phenyl]propan-1-one (*Journal of the American Chemical Society* 1994, 116(6), 2312-17, 2.8 g, 0.01 mol) in EtOH (30 ml). The solution was heated to reflux temperature for 18 hours. After cooling to RT, the solvent was evaporated under reduced pressure and the residue diluted with EtOAc (30 ml). The organic phase washed with water (3×20 ml), dried over Na$_2$SO$_4$ and concentrated. The crude reaction was then dissolved in EtOH (20 ml) and Raney Nickel (5 spoons) added. The reaction mixture was stirred for 2 days under a balloon of nitrogen and then filtered through a pad of celite. The filtrate was concentrated and purified by chromatography on silica gel eluting with 50% AcOEt/Hexane to afford the title compound (0.8 g, 28%); $^1$H NMR δ (ppm)(CDCl$_3$, 360 MHz): 7.64 (2 H, d, J=7.7 Hz), 7.47 (2 H, d, J=7.7 Hz), 7.32 (2 H, m), 7.22-7.19 (3 H, m), 4.00 (1 H, t, J=6.7 Hz), 2.73-2.57 (2 H, m), 2.07-2.00 (2 H, m).

Intermediate 4

N-[(1E,2E)-4,4-dimethylpent-2-en-1-ylidene]-2-methylpropane-2-sulfinamide

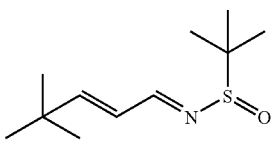

To a solution of 2-methylpropane-2-sulfinamide (3.08 g, 0.025 mol) in dichloromethane (10 ml) was added CuSO$_4$ (5.42 g, 0.034 mol) followed by (2E)-4,4-dimethylpent-2-enal (*Journal of Organic Chemistry* 1993, 58(9), 2517-22, 1.9 g, 0.017 mol) in dichloromethane (60 ml). The reaction mixture was stirred at RT overnight under nitrogen and then filtered through a pad of celite. The filtrate was evaporated under reduced pressure and purified by chromatography on silica gel eluting with 10% AcOEt/Hexane to give 2.1 g (58%) of the title compound; $^1$H NMR δ (ppm)(CDCl$_3$, 400 MHz): 8.19 (1 H, d, J=9.2 Hz), 6.53 (1 H, d, J=15.7 Hz), 6.36 (1 H, dd, J=9.2, 15.7 Hz), 1.21 (9 H, s), 1.12 (9 H, s).

Intermediate 5

4,4-Dimethyl-1-[4-(trifluoromethyl)phenyl]pentan-1-amine

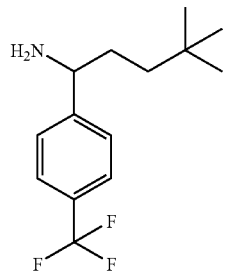

Step 1

Bromo[4-(trifluoromethyl)phenyl]magnesium (0.46M in Et$_2$O, 20 ml, 9.3 mmol) was added dropwise to a solution of intermediate 4 (1.0 g, 4.65 mmol) in dichloromethane (20 ml) at −60° C. under nitrogen. The mixture was allowed to slowly warm to RT (over 3 hours) and then quenched with a saturated solution of NH$_4$Cl (20 ml). The product was extracted with dichloromethane (20 ml), dried over Na$_2$SO$_4$ and concentrated. Purification by chromatography on silica gel eluting with 30% AcOEt/Hexane afforded N-{(2E)-4,4-dimethyl-1-[4-(trifluoromethyl)phenyl]pent-2-en-1-yl}-2-methylpropane-2-sulfinamide (1.2 g, 71%); $^1$H NMR δ (ppm)(CDCl$_3$, 400 MHz): 7.61 (2 H, d, J=8.1 Hz), 7.46 (2 H, d, J=8.1 Hz), 5.83 (1 H, dd, J=0.7, 15.6 Hz), 5.38 (1 H, dd, J=7.9, 15.6 Hz), 4.97 (1 H, dd, J=2.8, 7.9 Hz), 3.42 (1 H, bd), 1.23 (9 H, s), 1.01 (9 H, s).

Step 2

HCl (4.0N in dioxane, 4.1 ml, 0.017 mol) was added to a solution of the sulfinamide from the foregoing step (1.2 g, 3.3 mmol) in dry MeOH (20 ml) at 0° C. and the reaction mixture was stirred at that temperature for 3 hours. After evaporation of the solvent under reduced pressure, the residue was dissolved in dichloromethane (20 ml), washed with a saturated solution of NaHCO$_3$ (20 ml), brine (20 ml), dried over Na$_2$SO$_4$ and concentrated. Purification by chromatography on silica gel eluting with a gradient 10-25% AcOEt/Hexane afforded (2E)-dimethyl-1-[4-(trifluoromethyl)phenyl]pent-2-en-1-amine (0.62 g, 73%); $^1$H NMR δ (ppm)(CDCl$_3$, 360 MHz): 7.58 (2 H, d, J=8.2 Hz), 7.47 (2 H, d, J=8.2 Hz), 5.70 (1 H, dd, J=1.0, 15.5 Hz), 5.47 (1 H, dd, J=6.8, 15.5 Hz), 4.54 (1 H, d, J=6.8 Hz), 1.01 (9 H, s).

Step 3

The olefin from the foregoing step (0.1 g, 0.39 mmol) was dissolved in MeOH (5 ml) and Pd/C 10% wt (4 mg) was added. The reaction mixture was stirred for 12 hours in a Parr at 40 PSI. The mixture was filtered trough a pad of celite and the filtrate was then concentrated under reduced pressure. Purification by chromatography on silica gel eluting with a gradient 20-50% AcOEt/Hexane afforded the desired 4,4-dimethyl-1-[4-(trifluoromethyl)phenyl] pentan-1-amine (90 mg, 89%) as a colourless oil; $^1$H NMR δ (ppm)(CDCl$_3$, 360 MHz): 7.60 (2 H, d, J=8.1 Hz), 7.45 (2 H, d, J=8.1 Hz), 3.91 (1 H, t, J=6.8 Hz), 1.67-1.62 (4 H, m), 0.87 (9 H, s).

Intermediate 6

1-[2,4-Bis(trifluoromethyl)phenyl]butan-1-amine

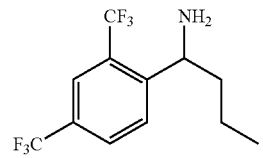

Step 1

A mixture of 2,4-bis trifluoromethyl benzaldehyde (10.0 g, 41.3 mmol), tert butyl sulfinamide (4.5 g, 37.2 mmol) and anhydrous CuSO$_4$ (13.1 g, 82.6 mmol) in DCM (100 ml) was stirred at room temperature overnight. The fine suspension was diluted with water and extracted with DCM. The extracts were washed with water, dried (MgSO$_4$) and evaporated in vacuo to afford the desired N-{(1E)-[2,4-bis(trifluoromethyl)phenyl]methylene}-2-methylpropane-2-sulfinamide as an off white solid (7.62 g, 53%), with no further purification. $^1$H NMR δ (ppm)(CDCl$_3$): 8.99 (1 H, d, J=1.9 Hz), 8.35 (1 H, d, J=8.2 Hz), 8.02 (1 H, s), 7.92 (1 H, d, J=8.2 Hz), 1.28 (9 H, d, J=4.6 Hz); m/z (ES$^+$) 346 (MH$^+$).

Step 2

A solution of N-{(1E)-[2,4-bis(trifluoromethyl)phenyl]methylene}-2-methylpropane-2-sulfinamide (7.62 g, 22.0 mmol) in DCM (50 ml) at −78° C. was treated with ″propyl magnesium chloride (2M in DCM, 16.5 ml, 33.1 mmol). The resultant mixture was allowed to warm to room temperature over 16 hours. NH$_4$Cl solution (saturated, 80 ml) was added and the solution was extracted with DCM. The extracts were washed with brine, dried (MgSO$_4$) and evaporated in vacuo to a yellow oil (3.9 g). The oil was dissolved in dry methanol (200 ml) cooled to 0° C. and treated with HCl (4N in dioxane, 10.0 ml, 40.1 mmol). The solution was stirred at 0° C. for 90 minutes before the solvent was evaporated in vacuo. The residue was made basic (NaHCO$_3$, saturated) and extracted with DCM. The extracts were dried (MgSO$_4$) and evaporated in vacuo to a yellow oil which was purified by chromatography (silica, 10-50% EtOAc/isohexane) to give the amine as a pale oil (1.75 g, 28%); $^1$H NMR δ (ppm)(CDCl$_3$): 7.87 (1 H, s), 7.88 (1 H, d, J=9.6 Hz), 7.81 (1 H, d, J=9.6 Hz), 4.42-4.39 (1 H, m), 1.55 (2 H, br), 1.68 (2 H, d, J=7.9 Hz), 1.30-1.16 (2 H, m), 0.95-0.89 (3 H, m); m/z (ES$^+$) 286 (MH$^+$).

Intermediate 7

1-[2,5-Bis(trifluoromethyl)phenyl]butan-1-amine

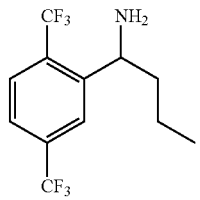

Step 1

A mixture of 2,5-bis trifluoromethyl benzaldehyde (21.5 g, 88.8 mmol), tert butyl sulfinamide (16.1 g, 133 mmol) and anhydrous CuSO$_4$ (16.5 g, 103 mmol) in DCM (94 ml) was stirred at room temperature for 16 hours and at reflux for 3 days. The fine suspension was diluted with water and extracted with DCM. The extracts were washed with water, dried (MgSO$_4$) and evaporated in vacuo to an off white solid which was purified by chromatography (silica, 4-10% EtOAc/isohexane) to give the desired N-{(1E)-[2,5-bis(trifluoromethyl)phenyl]methylene}-2-methylpropane-2-sulfinamide as a white crystalline solid (14.8 g, 91%); $^1$H NMR δ (ppm)(CDCl$_3$): 8.98 (1 H, d, J=1.8 Hz), 8.46 (1 H, s), 7.92-7.85 (2 H, m), 1.29 (9 H, s); m/z (ES$^+$) 346 (MH$^+$).

Step 2

A solution of N-{(1E)-[2,5-bis(trifluoromethyl)phenyl]methylene}-2-methylpropane-2-sulfinamide (6.7 g, 19.4 mmol) in DCM (50 ml) at −78° C. was treated with "propyl magnesium chloride (2M in DCM, 15 ml, 29 mmol) using the procedure of Intermediate 6, step 2, to give the desired amine as a pale oil (5.1 g, 94%). $^1$H NMR δ (ppm)(CDCl$_3$): 8.02 (1 H, s), 7.74 (1 H, d, J=8.2 Hz), 7.59 (1 H, d, J=8.3 Hz), 4.43-4.41 (1 H, m), 1.72 (2H, br), 1.68 (2 H, d, J=7.9 Hz), 1.30-1.16 (2 H, m), 0.95-0.89 (3 H, m); m/z (ES$^+$) 286 (MH$^+$).

Intermediate 8

(1S)-4-methyl-1-[4-(trifluoromethyl)phenyl]pentyl}amine

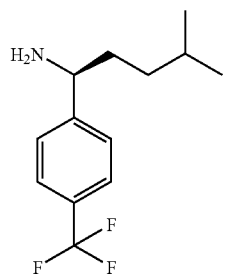

Step 1

Magnesium (17 g) was stirred 10 mins under nitrogen then tetrahydrofuran (400 ml) was added. A 5 ml portion of bromomethylbutane was added and the mixture stirred 5 minutes until the reaction initiated (exotherm) the reminder of the bromomethylbutane (100 g, 0.672 mol) was added keeping the temp below 35° C. (water bath). The mixture was stirred 1 hr at rt and a solution of 4-CF$_3$-benzonitrile (10 g, 0.584 mol) in toluene (11) containing some CuBr was added dropwise keeping the temp 25° C. The solution was stirred 1 h and quenched carefully with 15% H$_2$SO$_4$ (exotherm). The organic layer was decanted, washed with brine, dried over MgSO$_4$ and concentrated in vacuo. The oil was purified by column chromatography on silica using isohexane as eluent to give 4-methyl-1-[4-(trifluoromethyl)phenyl]pentan-1-one (126 g) which solidified on standing. $^1$H NMR δ (ppm)(CDCl$_3$): 8.06 (2 H, d, J=8.1 Hz), 7.73 (2 H, d, J=8.1 Hz), 2.99 (2 H, app. t, J=7.4 Hz), 1.68-1.60 (3 H, m), 0.96 (6 H, d, J=6.3 Hz).

Step 2

To a solution of 4-methyl-1-[4-(trifluoromethyl)phenyl]pentan-1-one (70 g, 0.312 mol) in toluene (500 ml) at room temperature was added S-phenylethylamine (44.5 g, 0.374 mol) and zinc chloride (2 g, 15.61 mmol). A Dean Stark apparatus was attached and the reaction refluxed for 16 h. The reaction was cooled down, washed with 1N NaOH (800 ml), three times with saturated ammonium chloride, dried over magnesium sulfate and evaporated to give 4-methyl-1-[4-(trifluoromethyl)phenyl]pentylidene}[(1S)-1- phenylethyl]amine (87 g) as a 3:1 mixture of isomers as an oil that was taken directly into Step 3.

Step 3

To a solution of 4-methyl-1-[4-(trifluoromethyl)phenyl]pentylidene}[(1S)-1-phenylethyl]amine (87 g, 0.25 mol) in methanol (0.51) at −20° C. was added sodium borohydride (10 g, 0.263 mol) portionwise. The solution was stirred ½ hrs at 0° C. and quenched carefully with 1N HCl, basified with 4N NaOH and extracted with ethyl acetate. The organic layer was decanted, dried (MgSO$_4$) and evaporated to give 85 g of 4-methyl-1-[4-(trifluoromethyl)phenyl]pentyl}[(1S)-1-phenylethyl] amine as a 3/1 mixture of diastereomers by NMR. This was dissolved in methanol (250 ml) and phthalic acid (40 g) was added. The solution was stirred at room temperature when it started to crystallise. The mixture was stirred 2 hrs at room temperature and the solid was then filtered to give single diastereomer {(1R)-4-methyl-1-[4-(trifluoromethyl)phenyl]pentyl}[(1S)-1-phenylethyl] amine as the phthalic acid salt (70.5 g). A small portion of the phthalic acid salt was partitioned between CDCl$_3$ and aqueous K$_2$CO$_3$ to form the free base and a $^1$H NMR was taken; $^1$H NMR δ (ppm)(CDCl$_3$): 7.57 (2 H, d, J=8.0 Hz), 7.33 (5 H, dd, J=7.6, 9.8 Hz), 7.16 (2 H, d, J=6.9 Hz), 3.40 (1 H, q, J=6.7 Hz), 3.32 (1 H, t, J=6.9 Hz), 1.66-1.48 (2 H, m), 1.46-1.32 (1 H, m), 1.26 (3 H, d, J=6.7 Hz), 1.19-1.09 (1 H, m), 0.95-0.85 (1 H, m), 0.79 (3 H, d, J=3.6 Hz), 0.77 (3 H, d, J=3.5 Hz).

Step 4

A suspension of {(1R)-4-methyl-1-[4-(trifluoromethyl)phenyl]pentyl}[(1S)-1-phenylethyl] amine phthalate salt (70 g, 0.135 mol) and 10% palladium on carbon (900 mg) in EtOH (300 ml) was hydrogenated under 40 psi at 57° C. for 3.5 h. The catalyst was filtered and the solution concentrated to a half. The organic was diluted with ethyl acetate, washed three times with 4N NaOH then with brine, dried (MgSO$_4$) and evaporated to give the title compound as a liquid (60 g); $^1$H NMR δ (ppm)(CDCl$_3$): 7.58 (2 H, d, J=8.2 Hz), 7.43 (2 H, d, J=8.0 Hz), 3.93 (1 H, t, J=6.8 Hz), 1.69-1.59 (2 H, m), 1.57-1.49 (1 H, m), 1.28-1.18 (1 H, m), 1.11-1.01 (1 H, m), 0.87 (3 H, d, J=1.8 Hz), 0.85 (3 H, d, J=1.8 Hz); m/z (ES$^+$) 246 (M+H$^+$). $\alpha_D^{20}$=−9.0 (c=1, CHCl$_3$).

The enantiomer (+)-{(1R)-4-methyl-1-[4-(trifluoromethyl)phenyl]pentyl}amine was prepared by analogy to intermediate 8 but employing R-phenylethylamine instead of S-phenylethylamine in Step 2.

Intermediate 9

{(1S)-1-[4-(trifluoromethyl)phenyl]butyl}amine

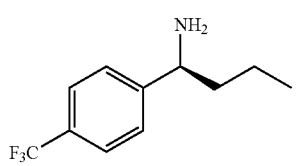

{(1S)-1-[4-(trifluoromethyl)phenyl]butyl}amine was prepared by analogy to Intermediate 8, by use of n-propylbromide in Step 1; $^1$H NMR δ (ppm)(CDCl$_3$): 7.58 (2 H, d, J=8.1 Hz), 7.43 (2 H, d, J=8.1 Hz), 3.97 (1 H, t, J=6.9 Hz), 1.68-1.60 (2 H, m), 1.50 (2 H, s), 1.36-1.21 (2 H, m), 0.91 (3 H, t, J=7.3 Hz).

Intermediate 10

{(1R)-1-[4-(trifluoromethyl)phenyl]butyl}amine

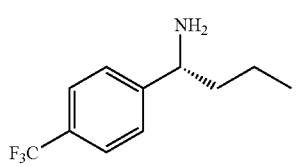

{(1R)-1-[4-(trifluoromethyl)phenyl]butyl}amine was prepared as intermediate 9 employing R-phenylethylamine instead of S-phenylethylamine in Step 2; $^1$H NMR δ (ppm) (CDCl$_3$): 7.58 (2 H, d, J=8.1 Hz), 7.43 (2 H, d, J=8.1 Hz), 3.97 (1 H, t, J=6.9 Hz), 1.68-1.60 (2 H, m), 1.50 (2 H, s), 1.36-1.21 (2 H, m), 0.91 (3 H, t, J=7.3 Hz).

Intermediate 11

{(1R)-1-[4-(trifluoromethyl)phenyl]pentyl}amine

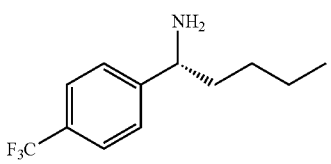

{(1R)-1-[4-(trifluoromethyl)phenyl]pentyl}amine was prepared by analogy to Intermediate 8, by use of n-butylbromide in Step 1 and employing R-phenylethylamine instead of S-phenylethylamine in Step 2; $^1$H NMR δ (ppm)(CDCl$_3$): 7.55 (2 H, d, J=8.2 Hz), 7.43 (2 H, d, J=8.2 Hz), 3.95 (1 H, t, J=6.9 Hz), 1.71-1.67 (2 H, m), 1.37-1.13 (4 H, m), 0.87 (3 H, t, J=7.1 Hz).

Intermediate 12

(2R,3S)-2-allyl-3-ethylcyclohexanone

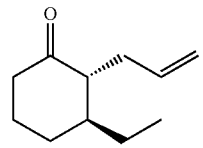

Prepared according to *Chem. Comm.*, 2001, 735-736

Intermediate 13

[(1R,2S)-2-ethyl-6-oxocyclohexyl]acetic acid

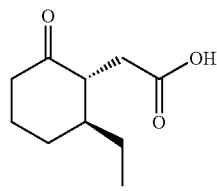

To a bi-phasic solution of intermediate 12 (1.09 g, 6.57 mmol) and sodium periodate (5.76 g, 26.93 mmol) in carbon tetrachloride (13 ml), acetonitrile (13 ml) and water (19.5 mL) was added ruthenium trichloride monohydrate (32 mg, 8.14 mmol). The resulting heterogeneous solution was stirred at ambient temperature for 16 h. The reaction mixture was diluted with dichloromethane (100 ml) and filtered through hyflo supercel. The filtrate was partitioned between dichloromethane and aqueous. The aqueous layer was further extracted with dichloromethane (5×50 ml). The combined organic extracts were washed with brine, dried over MgSO$_4$ and concentrated in vacuo to give the title compound as an oil (1.0 g, 83%) 1H NMR δ (ppm)(400 MHz, CDCl$_3$): 9.84-9.79 (s, 1H), 2.87-2.74 (m, 1H), 2.72-2.62 (m, 1H), 2.46-2.32 (m, 3H), 2.14-2.04 (m, 1H), 1.99-1.97 (m, 1H), 1.67-1.41 (m, 4H), 1.38-1.23 (m, 1H), 0.94-0.90 (m, 3H).

Intermediate 14

Ethyl [(1R,2S)-2-ethyl-6-oxocyclohexyl]acetate

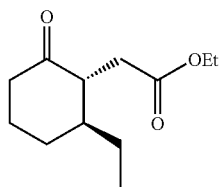

A catalytic amount of concentrated hydrochloric acid was added into a solution of intermediate 13 (1.0 g, 5.43 mmol) in ethanol (50 ml). The resulting solution was stirred at reflux for 16 h. The reaction mixture was concentrated in vacuo and the residual oil was purified by flash chromatography eluting with 10% ethyl acetate in hexane to afford ethyl [(1R,2S)-2-ethyl-6-oxocyclohexyl]acetate as a colourless oil (911 mg, 80%). $^1$H NMR δ (ppm)(400 MHz, CDCl$_3$): 4.16-4.09 (2 H, m), 2.70-2.61 (2H, m), 2.44-2.32 (m, 3H), 2.13-2.07 (m, 1H), 1.97-1.91 (m, 1H), 1.65-1.34 (m, 3H), 1.33-1.21 (m, 5H), 0.93 (t J 7.4 Hz, 3H)

Intermediate 15

(2E)-4,4-dimethylpent-2-en-1-ol

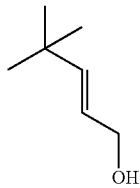

Prepared as in *J Org. Chem.* 2003, 68(8), 3130-3138. $^1$H NMR δ (ppm)(400 MHz, CDCl$_3$): 1H NMR δ (ppm)(CDCl$_3$): 5.71 (1 H, d, J=15.9 Hz), 5.54 (1 H, dt, J=15.9, 6.0 Hz), 4.10 (2 H, d, J=6.0 Hz), 1.02 (9 H, s).

Intermediate 16

2-Isopropylprop-2-en-1-ol

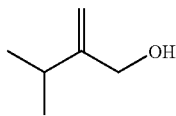

Prepared according to the procedure described in *J. Organomet. Chem.* 1979, 168(1), 1-11. $^1$H NMR δ (ppm)(400 MHz, CDCl$_3$): 1H NMR δ (ppm)(CDCl$_3$): 5.00 (1 H, d, J=1.2 Hz), 4.90 (1 H, t, J=1.0 Hz), 4.13 (2 H, s), 2.36-2.28 (1 H, m), 1.43 (1 H, s), 1.07 (6 H, d, J=6.9 Hz).

Intermediate 17

2-cyclohexylprop-2-en-1-ol

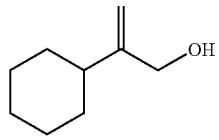

Prepared according to the procedure described in *J. Organomet. Chem.* 1979, 168(1), 1-11. $^1$H NMR δ (ppm)(400 MHz, CDCl$_3$): 5.00 (1 H, s), 4.87 (1 H, s), 4.11 (2 H, s), 1.95 (1 H, t, J=11.2 Hz), 1.74-0.90 (10 H, m).

Intermediate 18

2-[4-(trifluoromethyl)phenyl]prop-2-en-1-ol

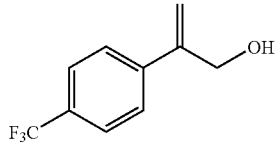

Prepared according to the procedure described in *J. Organomet. Chem.* 1979, 168(1), 1-11. $^1$H NMR δ (ppm)(400 MHz, CDCl$_3$): 7.58 (4 H, q, J=8.6 Hz), 5.55 (1 H, s), 5.46 (1 H, s), 4.53 (2 H, dd, J=0.0, 5.9 Hz), 1.77 (1 H, t, J=6.0 Hz).

Intermediate 19

(2E)-3-(2,4-dichlorophenyl)prop-2-en-1-ol

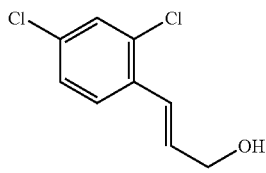

Step 1

To a stirred solution of (2E)-3-(2,4-Dichlorophenyl) acrylic acid (10 g, 46 mmol) in ethanol (60 ml) was added conc. H$_2$SO$_4$ (2.5 ml). The mixture was heated to reflux and for 48 H, then allowed to cool, concentrated in vacuo, dissolved in ethyl acetate, washed three times with 4N NaOH, dried over sodium sulfate and concentrated in vacuo to afford ethyl (2E)-3-(2,4-dichlorophenyl)acrylate (10.7 g) as pale brown crystals. $^1$H NMR δ (ppm)(CDCl$_3$): 8.00 (1 H, d, J=16.1 Hz), 7.55 (1 H, d, J=8.5 Hz), 7.44 (1 H, d, J=1.9 Hz), 7.26 (1 H, dd, J=2.0, 8.4 Hz), 6.41 (1 H, d, J=16.1 Hz), 4.28 (2 H, q, J=7.1 Hz), 1.34 (3 H, t, J=7.1 Hz).

Step 2

To a stirred solution of ethyl (2E)-3-(2,4-dichlorophenyl) acrylate (11.3 g, 46 mmol) in tetrahydrofuran at −10° C. was added diisobutylaluminium hydride (1.0 M in toluene, 100 ml, 0.11 mol) dropwise. After addition was complete, the reaction was cooled to −78° C. and methanol (40 ml) added dropwise. Ammonium chloride (sat. aq., 70 ml) was then added and the reaction allowed to warm to 0° C. After 15 min at 0° C. the reaction was allowed to warm to room temperature and stirred for 1 h. The mixture was then filtered through a pad of hyflo supercel (washing well with ethyl acetate) and the concentrated to give the title compound (7.8 g) as pale yellow crystals. $^1$H NMR δ (ppm)(CDCl$_3$): 7.44 (1 H, d, J=8.4 Hz), 7.36 (1 H, d, J=2.0 Hz), 7.19 (1 H, dd, J=2.0, 8.5 Hz), 6.93 (1 H, d, J=15.8 Hz), 6.36-6.28 (1 H, m), 4.35 (2 H, d, J=5.4 Hz), 1.84 (1 H, s).

Intermediate 20

(2E)-3-(4-Chlorophenyl)-2-isopropylprop-2-en-1-ol

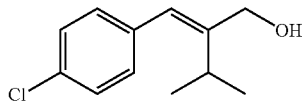

Prepared according to a procedure described in PCT Int. Appl. (2002), 34 pp., WO 2002002487. $^1$H NMR δ (ppm) (CDCl$_3$): 7.30 (2 H, d, J=8.4 Hz), 7.15 (2 H, d, J=8.4 Hz), 6.49 (1 H, s), 4.30 (2 H, s), 3.07-2.99 (1 H, m), 1.09 (6 H, d, J=7.0 Hz).

Intermediate 21

Mixture of Ethyl (2-ethoxycyclohex-2-en-1-yl)acetate and ethyl (2,2-diethoxycyclohexyl)acetate

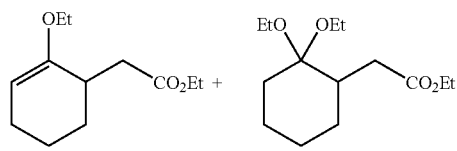

To a stirred solution of ethyl (2-oxocyclohexyl)acetate (40.2 ml, 0.228 mol) in ethanol (66 ml) was added p-toluenesulfonic acid (422 mg, 2.28 mmol) and triethylorthoformate (113 ml, 0.684 mol). The reaction mixture was heated to 95° C. and stirred for 16 h. The mixture was concentrated in vacuo at 60° C. for 2½ hours to remove triethylorthoformate. The mixture was used crude in subsequent reactions. $^1$H NMR δ (ppm)(CDCl$_3$): 4.60 (1 H, t, J=3.9 Hz), 4.17-4.09 (4 H, m), 3.76-3.58 (4 H, m), 3.47-3.41 (3 H, m), 3.11 (1 H, s), 2.71-2.63 (2 H, m), 2.58-2.40 (1 H, m), 2.37-2.09 (4 H, m), 2.07-1.97 (4 H, m), 1.91-1.33 (8 H, m), 1.31-1.16 (14 H, m).

Intermediate 22

{(1R)-3-methyl-1-[4-(trifluoromethyl)phenyl]butan-1-amine

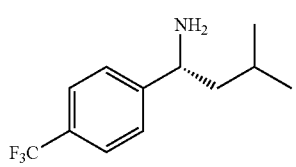

{(1R)-3-methyl-1-[4-(trifluoromethyl)phenyl]butan-1-amine was prepared by analogy to Intermediate 8, by use of i-butylbromide in Step 1 and employing R-phenylethylamine instead of S-phenylethylamine in Step 2; $^1$H NMR δ (ppm) (CDCl$_3$): 7.58 (2 H, d, J=8.1 Hz), 7.43 (2 H, d, J=8.2 Hz), 4.03 (1 H, t, J=6.8 Hz), 1.34-1.22 (3 H, m), 0.93 (3 H, d, J=6.3 Hz), 0.91 (3 H, d, J=6.3 Hz).

Intermediate 23

{1-[4-(trifluoromethyl)phenyl]butyl}hydrazine

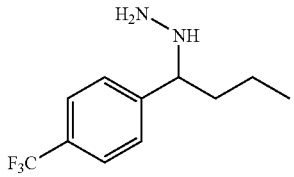

Hydrazine monohydrate (8.9 g) was dissolved in isopropanol (25 ml) and 1-(1-bromobutyl)-4-(trifluoromethyl)benzene (as prepared in WO 2005013985, 2.0 g, 7.12 mmol) added. The mixture was heated to 70° C. and stirred for 16 h. After this time the solvent was removed and the residue taken up in ethyl acetate and washed three times (H$_2$O). The combined organics were dried (sodium sulfate) and concentrated to give the mixture of products as a white solid suspended in a clear oil. The mixture was triturated with diethyl ether to give a white solid; 1H NMR δ (ppm)(DMSO): 9.20 (1 H, s), 7.76 (2 H, d, J=8.1 Hz), 7.64 (2 H, s), 4.16 (1 H, s), 1.85 (1 H, s), 1.59 (1 H, s), 1.20-0.96 (2 H, m), 0.82 (3 H, t, J=7.3 Hz).

Example 1

(3-phenyl-1-{1-[4-(trifluoromethyl)phenyl]butyl}-4,5,6,7-tetrahydro-1H-indol-7-yl)acetic acid

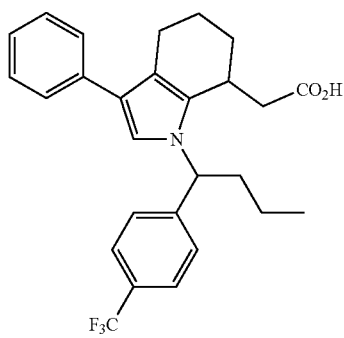

Step 1

Ethyl 2-cyclohexanoneacetate (0.34 ml, 1.92 mmol) was added to a solution of Intermediate 1 (418 mg, 1.92 mmol) in toluene (10 ml) in a flask fitted with Dean-Stark apparatus. The reaction was heated to reflux under N$_2$ for 16 h, then allowed to cool to room temperature. The resulting solution of ethyl [(2E)-2-({1-[4-(trifluoromethyl)phenyl]butyl}imino)cyclohexyl]acetate in toluene was used directly in the next step.

Step 2

Trans-beta-nitrostyrene (286 mg, 1.92 mmol) was added to the reaction mixture, the Dean-Stark trap was replaced with a reflux condenser and the reaction heated at reflux for 40 h. After cooling, the reaction was diluted with ethyl acetate, washed with saturated sodium bicarbonate solution and twice with water, then dried over sodium sulfate and concentrated in vacuo. The product was purified by mass directed HPLC to give ethyl (3-phenyl-1-{1-[4-(trifluoromethyl)phenyl]butyl}-4,5,6,7-tetrahydro-1H-indol-7-yl)acetate (107 mg, 11%), a colourless oil as a 1:1 mixture of diastereomers.

Step 3

To a stirred solution of ethyl (3-phenyl-1-{1-[4-(trifluoromethyl)phenyl]butyl}-4,5,6,7-tetrahydro-1H-indol-7-yl)acetate (107 mg, 2.2 mmol) in dioxane (5 ml) and water (0.5 ml) was added lithium hydroxide (900 mg, 22.0 mmol) and the reaction heated to reflux for 16 h. After cooling, the reaction was diluted with ethyl acetate and acidified with 2N HCl. The aqueous layer was extracted three times with ethyl acetate, and the combined organic layers dried over sodium sulfate and concentrated in vacuo. The product was purified by mass directed HPLC to give (3-phenyl-1-{1-[4-(trifluoromethyl)phenyl]butyl}-4,5,6,7-tetrahydro-1H-indol-7-yl)acetic acid (55.1 mg, 55%), a colourless foam as a 1:1 mixture of diastereomers A and B; $^1$H NMR δ (ppm) (CDCl$_3$): 7.59 (2 H, d, J=8.2 Hz, A/B), 7.53 (2 H, d, J=8.1 Hz, A/B), 7.47 (2 H, d, J=8.1 Hz, A/B), 7.35 (4 H, t, J=7.3 Hz A+B), 7.21-7.13 (4 H, m, A+B), 7.06 (1 H, s, A), 6.95 (1 H, s, B), 5.19-5.11 (2 H, m, A+B), 3.39 (1 H, d, J=9.0 Hz, B), 3.06 (1 H, s, A), 2.79-2.65 (5 H, m, A+B), 2.37-2.19 (2 H, m, A+B), 2.14-2.08 (4 H, m, A+B), 2.00 (1 H, s, A/B), 1.90-1.78 (6 H, t, J=13.5 Hz, A+B), 1.74-1.70 (4 H, m, A+B), 1.42 (1 H, t, J=6.1 Hz, A/B), 1.38-1.30 (1 H, m A/B), 1.03 (3 H, t, J=7.3 Hz, A/B), 0.95 (3 H, t, J=7.3 Hz, A/B); m/z (ES$^-$) 454 (M−H$^+$).

Example 2

(3-(2,4-Dichlorophenyl)-1-{1-[4-(trifluoromethyl)phenyl]butyl}-4,5,6,7-tetrahydro-1H-indol-7-yl)acetic acid

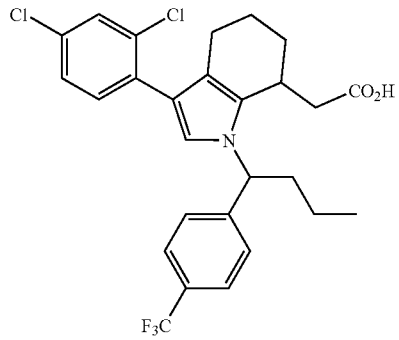

Prepared as described for Example 1, using 2,4-dichloro-beta-nitrostyrene in Step 2 with heating at 200° C. in a microwave apparatus; m/z (ES$^-$) 522 (M−H$^+$). The enantiomers and diastereomers could be separated by supercritical fluid chromatography. A CHIRALPAK AD-H column 250×10 mm (5µ) Column temperature 40° C., Mobile phase: 85/15 CO$_2$/MeOH, Flow rate: 10 mL/min, outlet pressure 100 bar gave pure Example 2a ((7S)-3-(2,4-dichlorophenyl)-1-{(1S)-1-[4-(trifluoromethyl)phenyl]butyl}-4,5,6,7-tetrahydro-1H-indol-7-yl)acetic acid eluting at 5.50 min $^1$H NMR δ (ppm) (CDCl$_3$): 7.55 (2 H, d, J=8.2 Hz), 7.46 (1 H, d, J=2.0 Hz), 7.29 (1 H, s), 7.22 (1 H, dd, J=2.1, 8.3 Hz), 7.14 (2 H, d, J=8.1 Hz), 7.04 (1 H, s), 5.14 (1 H, dd, J=6.3, 9.0 Hz), 3.04 (1 H, s), 2.66 (2 H, d, J=6.7 Hz), 2.42 (2 H, t, J=3.7 Hz), 2.24-2.16 (1 H, m), 2.11-2.04 (1 H, m), 1.81-1.66 (5 H, m), 1.42 (1 H, dd, J=0.0, 6.6 Hz), 1.21 (3 H, d, J=6.1 Hz), 1.01 (3 H, t, J=7.3 Hz), a mixture of Example 2b ((7S)-3-(2,4-dichlorophenyl)-1-{(1R)-1-[4-(trifluoromethyl)phenyl]butyl}-4,5,6,7-tetrahydro-1H-indol-7-yl)acetic acid and Example 2c ((7R)-3-(2,4-dichlorophenyl)-1-{(1S-1-[4-(trifluoromethyl)phenyl]butyl}-4,5,6,7-tetrahydro-1H-indol-7-yl)acetic acid eluting at 6.25 min and finally pure Example 2d ((7R)-3-(2,4-dichlorophenyl)-1-{(1R)-1-[4-(trifluoromethyl)phenyl]butyl}-4,5,6,7-tetrahydro-1H-indol-7-yl)acetic acid eluting at 7.35 min $^1$H NMR δ (ppm) (CDCl$_3$): 7.55 (2 H, d, J=8.2 Hz), 7.46 (1 H, d, J=2.0 Hz), 7.29 (1 H, s), 7.22 (1 H, dd, J=2.1, 8.3 Hz), 7.14 (2 H, d, J=8.1 Hz), 7.04 (1 H, s), 5.14 (1 H, dd, J=6.3, 9.0 Hz), 3.04 (1 H, s), 2.66 (2H, d, J=6.7 Hz), 2.42 (2 H, t, J=3.7 Hz), 2.24-2.16 (1 H, m), 2.11-2.04 (1 H, m), 1.81-1.66 (5 H, m), 1.42 (1 H, dd, J=0.0, 6.6 Hz), 1.21 (3 H, d, J=6.1 Hz), 1.01 (3 H, t, J=7.3 Hz). The mixture of Example 2b and Example 2c were separated by further SFC purification using a CHIRALCEL OJ-H column 250×10 mm (5µ) Column temperature 40° C., Mobile phase: 80/20 CO$_2$/MeOH, Flow rate: 10 mL/min, outlet pressure 100 bar gave Example 2b ((7R)-3-(2,4-dichlorophenyl)-1-{(1S)-1-[4-(trifluoromethyl)phenyl]butyl}-4,5,6,7-tetrahydro-1H-indol-7-yl)acetic acid eluting at 3.04 min $^1$H NMR δ (ppm)(CDCl$_3$): 7.59 (2 H, d, J=8.1 Hz), 7.46 (1 H, d, J=1.8 Hz), 7.32 (2 H, d, J=8.1 Hz), 7.30 (1 H, d, J=8.3 Hz), 7.22 (1 H, dd, J=8.3, 1.8 Hz), 6.96 (1 H, s), 5.18 (1 H, t, J=7.6 Hz), 3.38 (1 H, d, J=8.5 Hz), 2.48-2.43 (2 H, m), 2.29 (1 H, dd, J=11.0, 15.6 Hz), 2.12-2.06 (2 H, m), 2.03 (1 H, d, J=15.6 Hz), 1.88-1.76 (3 H, m), 1.68 (1 H, m), 1.38-1.30 (2 H, m), 0.96 (3 H, t, J=7.3 Hz) and Example 2c ((7S)-3-(2,4-dichlorophenyl)-1-{(1R)-1-[4-(trifluoromethyl)phenyl] butyl}-4,5,6,7-tetrahydro-1H-indol-7-yl)acetic acid eluting at 4.13 min $^1$H NMR δ (ppm) (CDCl$_3$): 7.59 (2 H, d, J=8.1 Hz), 7.46 (1 H, d, J=1.8 Hz), 7.32 (2 H, d, J=8.1 Hz), 7.30 (1 H, d, J=8.3 Hz), 7.22 (1 H, dd, J=8.3, 1.8 Hz), 6.96 (1 H, s), 5.18 (1 H, t, J=7.6 Hz), 3.38 (1 H, d, J=8.5 Hz), 2.48-2.43 (2 H, m), 2.29 (1 H, dd, J=11.0, 15.6 Hz), 2.12-2.06 (2 H, m), 2.03 (1 H, d, J=15.6 Hz), 1.88-1.76 (3 H, m), 1.68 (1 H, m), 1.38-1.30 (2 H, m), 0.96 (3 H, t, J=7.3 Hz).

Examples 3-16

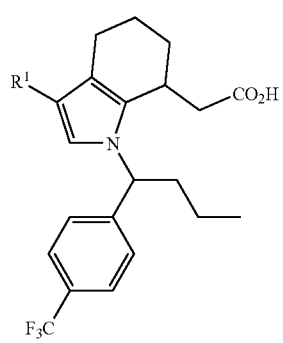

Following the procedures of Examples 1 and 2, using the appropriate nitroalkene in Step 2, the following were prepared:

| Example | R¹ | Mass Spec. (M – H⁺) |
|---|---|---|
| 3 | 4-isopropylphenyl | 496 |
| 4 | 4-methylphenyl | 468 |
| 5 | 2,6-dichlorophenyl | 522 |
| 6 | 2-CF₃-phenyl | 522 |
| 7 | 2-chlorophenyl | 488 |
| 8 | 4-chlorophenyl | 488 |
| 9 | 2-bromophenyl | 533 |
| 10 | 3-CF₃-phenyl | 522 |
| 11 | 3,4-dichlorophenyl | 522 |
| 12 | 3,5-dichlorophenyl | 522 |
| 13 | 2,3-dichlorophenyl | 522 |
| 14 | 2,5-dichlorophenyl | 522 |
| 15 | 2-Br-4-Cl-phenyl | 567 |
| 16 | 5-Cl-2-thienyl | 495 |

When not available commercially, the nitroalkenes were prepared by published methods, e.g. base-catalysed condensation of R¹CHO with nitromethane.

Example 17

(3-(2-butyl-4-chlorophenyl)-1-{1-[4-(trifluoromethyl)phenyl]butyl}-hydro-1H-indol-7-yl)acetic acid

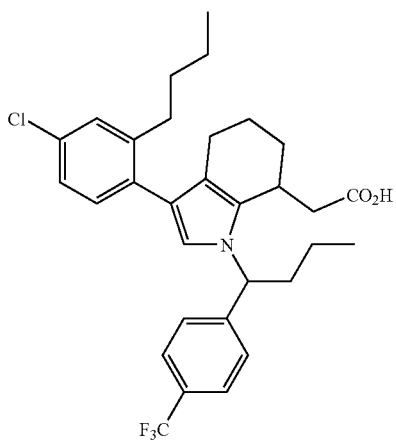

Ethyl (3-(2-bromo-4-chlorophenyl)-1-{1-[4-(trifluoromethyl)phenyl]butyl}-4,5,6,7-tetraydro-1H-indol-7-yl)acetate (prepared using the procedures of example 1, steps 1 and 2 using 2-bromo-4-chloro-1-[(E)-2-nitrovinyl]benzene in place of [(E)-2-nitrovinyl]benzene in step 1) (41 mg, 0.068 mmol) was dissolved in toluene (2 ml) and water (1 ml) and n-butylboronic acid (9 mg, 0.088 mmol), K₃PO₄ (51 mg, 0.24 mmol), tricylohexylphosphine (2 mg, 0.007 mmol), and palladium acetate (2 mg, 0.007 mmol) added. The mixture was degassed for 5 min, then heated to 100° C. and stirred for 2 h 30 min. The reaction was then allowed to cool, then diluted with water and extracted twice with ethyl acetate. The combined organics were washed with brine, dried over sodium sulfate, concentrated in vacuo and purified by column chromatography (1-10% EtOAc/Hexanes) to give the desired ester (12 mg) as a colourless oil.

This ester was hydrolysed following the procedure in Example 1 Step 3 to afford the desired acid; m/z (ES⁻) 544 (M–H⁺).

Example 18

(3-(2-(2-methylpropyl)-4-chlorophenyl)-1-{1-[4-(trifluoromethyl)phenyl]butyl}-4,5,6,7-tetrahydro-1H-indol-7-yl)acetic acid

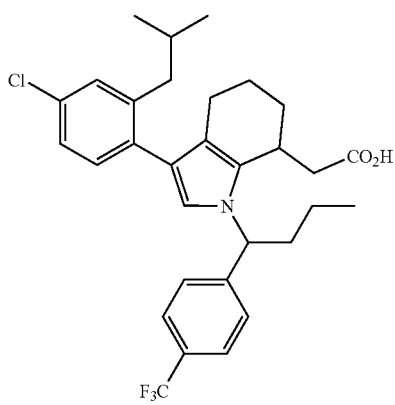

Prepared by analogy to example 17 using 2-methylpropylboronic acid in place of n-butylboronic acid; m/z (ES⁻) 544 (M–H⁺).

Example 19

(2-Phenyl-1-{1-[4-(trifluoromethyl)phenyl]butyl}-4,5,6,7-tetrahydro-1H-indol-7-yl)acetic acid

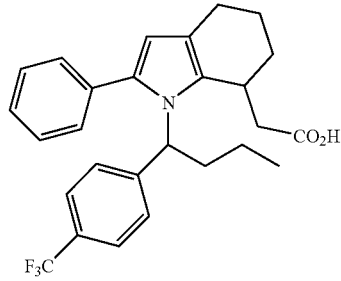

Step 1—Ethyl [2-oxo-3-(2-oxo-2-phenylethyl)cyclohexyl]acetate

Intermediate 2 (667 mg, 2.81 mmol) was dissolved in dimethylformamide (14 ml), 2-bromo-1-phenylethanone (560 mg, 2.81 mmol) was added and the reaction stirred for 24 h at room temperature. Water (5 ml) was added and the reaction allowed to stir for a further 24 h. The mixture was then diluted with ethyl acetate (100 ml) and washed with water. The aqueous fraction was re-extracted three times with ethyl acetate and the combined organic fractions washed three times with water, then dried over sodium sulfate, filtered and concentrated in vacuo. Column chromatography (10-20% ethyl acetate/hexanes) provided the title compound as a pale yellow oil (428 mg, 50%).

Step 2

The product of Step 1 (274 mg, 0.907 mmol), Intermediate 1 (195 mg, 0.907 mmol), acetic acid (0.1 ml) and toluene (10 ml) were refluxed for 16 hours in a Dean Stark apparatus. The reaction mixture was allowed to cool to RT, concentrated in vacuo, absorbed onto silica gel then purified by flash column chromatography (10% ethyl acetate/hexanes) to afford a colorless oil (35 mg, 8%) This product was hydrolysed by the method of example 1 Step 3 and purified by column chromatography (10-20% ethyl acetate/hexanes) to give the title compound, a colourless oil (18.3 mg, 55%) as a 2:1 mixture of diastereomers (designated isomers A and B respectively). $^1$H NMR δ (ppm) (CDCl$_3$): 7.56 (3 H, d, J=8.3 Hz, A+B), 7.49 (1 H, d, J=8.2 Hz A/B), 7.32-6.98 (14 H, m), 5.96 (1 H, s, B), 5.93 (1 H, s, A), 5.32-5.22 (2 H, m), 3.22 (1 H, d, J=10.9 Hz A), 3.10-2.96 (1 H, m, B), 2.69-2.49 (4 H, m, A+B), 2.40-2.26 (2 H, m, A+B), 2.22-2.08 (2 H, m, A+B), 2.03-1.89 (2 H, m, A+B), 1.86-1.71 (7 H, m, A+B) 1.6-1.1 (7 H, A+B) 0.97-0.78 (6 H, m, A+B); m/z (ES$^-$) 454 (M−H$^+$).

Example 20

(2-(2,4-dichlorophenyl)-1-{(1S)-1-[4-(trifluoromethyl)phenyl]butyl}-4,5,6,7-tetrahydro-1H-indol-7-yl)acetic acid

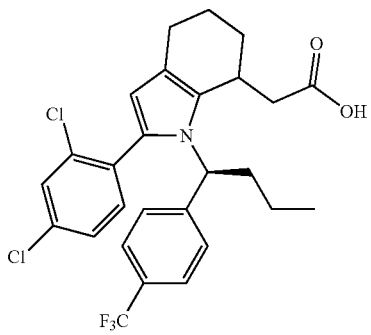

Prepared analogously to example 19, using 2-bromo-1-(2,4-dichlorophenyl)ethanone in step 1, desired product was obtained; m/z (ES$^-$) 522 (M−H$^+$).

Example 21

Example 21a ((7R)-2-tert-butyl-1-{(1S)-4-methyl-1-[4-(trifluoromethyl)phenyl]pentyl}-4,5,6,7-tetrahydro-1H-indol-7-yl)acetic acid and Example 21b ((7S)-2-tert-butyl-1-{(1S)-4-methyl-1-[4-(trifluoromethyl)phenyl]pentyl}-4,5,6,7-tetra hydro-1H-indol-7-yl)acetic acid

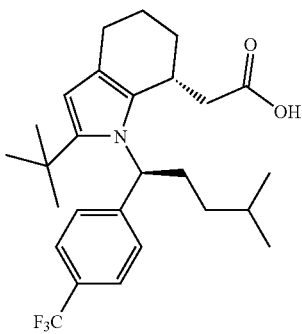

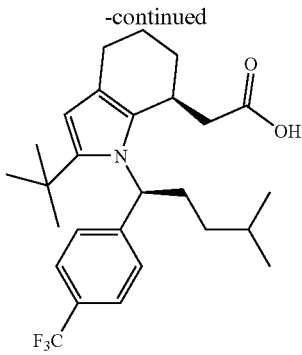

Step 1

Ethyl [3-(3,3-dimethyl-2-oxobutyl)-2-oxocyclohexyl]acetate

Prepared using procedure of Example 19 Step 1, using 1-bromo-3,3-dimethylbutan-2-one.

Step 2

A stirred solution of ethyl [3-(3,3-dimethyl-2-oxobutyl)-2-oxocyclohexyl]acetate (415 mg, 1.47 mmol) and {(1S)-4-methyl-1-[4-(trifluoromethyl)phenyl]pentyl}amine (432 mg, 1.76 mmol) in dichloromethane (10 ml) was cooled to −78° C. and triethylamine (1.2 ml, 8.82 mmol) then titanium tetrachloride (0.32 ml, 2.94 mmol) were added dropwise. The reaction became instantly dark brown on addition of titanium tetrachloride. The reaction was allowed to warm slowly to room temperature and then stirred for 16 h. The reaction mixture was quenched with saturated aqueous sodium bicarbonate, extracted three times with ethyl acetate, dried over sodium sulfate and purified by chromatography on silica gel eluting with 1-5% ethyl acetate/hexane afforded impure ethyl (2-tert-butyl-1-{(1S)-4-methyl-1-[4-(trifluoromethyl)phenyl]pentyl}-4,5,6,7-tetrahydro-1H-indol-7-yl)acetate (251 mg) which was taken into the next step without further purification; m/z (ES$^+$) 492 (M+H$^+$).

Step 3

The product from the foregoing step was dissolved in methanol (3 ml) and water (1 ml) and KOH (500 mg) added. The reaction mixture was heated to reflux and stirred for 16 h. After cooling, the reaction was quenched with 2N HCl and extracted three times with ethyl acetate, dried over sodium sulfate concentrated in vacuo and purified by chromatography on silica gel eluting with 20% ethyl acetate/hexane. Unhydrolysed starting ester (150 mg) was also recovered. The product was then further purified by Agilent mass directed HPLC, which also separated the diastereomers.

((7R)-2-tert-butyl-1-{(159-4-methyl-1-[4-(trifluoromethyl)phenyl]pentyl}-4,5,6,7-tetrahydro-1H-indol-7-yl)acetic acid $^1$H NMR δ (ppm) (CDCl$_3$): 7.55 (2 H, d, J=8.2 Hz), 7.34 (2 H, d, J=8.2 Hz), 5.80 (1H, s), 5.62 (1 H, t, J=7.4 Hz), 3.11 (1 H, d, J=10.8 Hz), 2.57-2.45 (3 H, m), 2.10-2.02 (1 H, m), 1.95 (1 H, dd, J=11.5, 17.0 Hz), 1.71-1.62 (3 H, m), 1.40 (9 H, s), 1.34-1.24 (3 H, m), 1.16-1.04 (2 H, s), 0.98-0.82 (6 H, m); m/z (ES$^-$) 462 (M−H$^+$).

((7S)-2-tert-butyl-1-{(1S)-4-methyl-1-[4-(trifluoromethyl)phenyl]pentyl}-4,5,6,7-tetrahydro-1H-indol-7-yl)acetic acid $^1$H NMR δ (ppm) (CDCl$_3$): 7.50 (2 H, d, J=8.3 Hz), 6.82 (2 H, d, J=8.2 Hz), 5.80 (1H, s), 5.53 (1 H, s), 2.64-2.52 (3 H, m), 2.25-2.13 (1 H, m), 2.02-1.98 (1 H, m), 1.74-1.54 (6 H, t, J=6.2 Hz), 1.41-1.38 (1 H, m), 1.34 (9 H, s), 1.21-1.13 (1 H, m), 1.16 (1H, d, J=7.2 Hz), 1.00 (3 H, d, J=6.3 Hz), 0.96 (3 H, d, J=6.3 Hz); m/z (ES) 462 (M−H$^+$).

Example 22

(2-Methyl-1-{1-[4-(trifluoromethyl)phenyl]butyl}-4,5,6,7-tetrahydro-1H-indol-7-yl)acetic acid

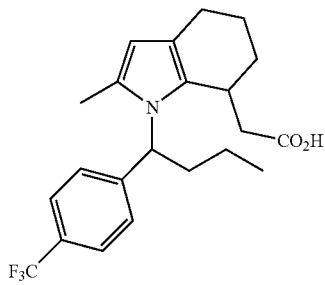

Step 1—Ethyl (2-oxo-3-prop-2-yn-1-ylcyclohexyl)acetate

Intermediate 2 (1.4 g, 6 mmol) was dissolved in toluene (7 ml) and propargyl bromide (80% wt in toluene, 7 ml) was added. The reaction was heated to 80° C. and stirred at this temperature for 16 h. Water (5 ml) was then added and the reaction refluxed for a further 2 h. After cooling, 2N HCl was added, and the mixture extracted three times with ethyl acetate, dried over sodium sulfate, filtered, concentrated in vacuo and purified by column chromatography (2.55-10% EtOAc/hexanes). The title compound was obtained as a 1:1 inseparable mixture with ethyl 2-cyclohexanoneacetate (550 mg).

Step 2

The product from Step 1 (250 mg) was dissolved in toluene (15 ml) and Intermediate 1 (300 mg) and acetic acid (1 drop) added. A Dean Stark apparatus was fitted and the reaction heated to reflux for 16 h. The reaction mixture was allowed to cool, concentrated in vacuo and purified by column chromatography to afford a colourless oil (13 mg). This product was hydrolysed by the method of Example 1 Step 3 and purified by column chromatography (10-30% EtOAc/hexanes) to give the title compound, a colourless oil (6.2 mg), as a 1.8:1 mixture of diastereomers. $^1$H NMR δ (ppm)(CDCl$_3$): 7.54 (4H, m, A+B), 7.15 (2 H, d, J=8.2 Hz, A), 7.03 (2 H, d, J=7.9 Hz, B), 5.72 (1 H, s, A), 5.69 (1H, s, B), 5.30-5.15 (2 H, m, A+B), 3.26 (2 H, m, A+B), 2.55-2.40 (4 H, m), 2.38-2.28 (2H, m), 2.26-2.20 (2H, m), 2.16-2.06 (2H, m), 2.02 (3H, s, B), 1.86 (3H, s, B), 1.84-1.74 (4H, m), 1.58-1.52 (2H, m) 1.40-0.80 (14H, m).

Example 23

(2-Ethyl-1-{(1R)-1-[4-(trifluoromethyl)phenyl]butyl}-4,5,6,7-tetrahydro-1H-indol-7-yl)acetic acid

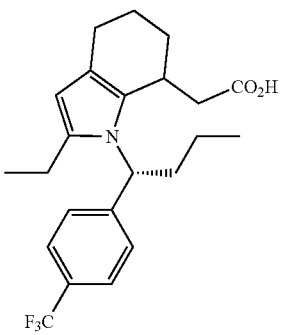

Step 1—Ethyl {3-[(2E)-but-2-en-1-yl]-2-oxocyclohexyl}acetate

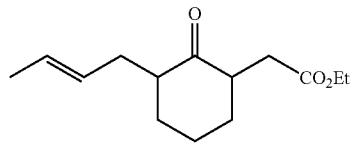

Intermediate 2 (6.4 g, 27 mmol) was dissolved in dimethylformamide (100 ml) and crotyl bromide (12 g, 90 mmol) was added. The reaction stirred at room temperature for 16 h. Water (24 ml) was then added and the reaction stirred for a further 5 d. Water (100 ml) was then added, and the mixture extracted three times with ethyl acetate, the combined organic phases washed three times with water, dried over sodium sulfate, filtered, concentrated in vacuo and purified by column chromatography (5-10% EtOAc/hexanes). The title compound (1.3 g) was obtained as a colourless oil as a mixture of diastereomers. $^1$H NMR δ (ppm)(CDCl$_3$): 5.49-5.33 (2 H, m), 4.13 (2 H, q, J=7.1 Hz), 2.92-2.74 (2 H, m), 2.48-2.32 (2 H, m), 2.21-2.11 (3 H, m), 1.92-1.70 (3 H, m), 1.67-1.58 (3 H, m), 1.41-1.23 (5 H, m).

Step 2—Ethyl (2-ethyl-7a-hydroxyoctahydro-1-benzofuran-7-yl)acetate

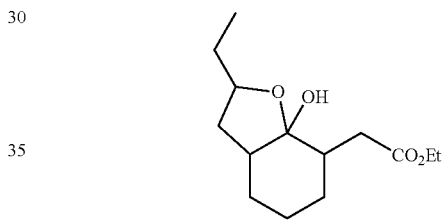

To a stirred solution of ethyl {3-[(2E)-but-2-en-1-yl]-2-oxocyclohexyl}acetate (565 mg, 2.37 mmol) in tetrahydrofuran (20 ml) at 0° C. was added borane.tetrahydrofuran complex (1 M in tetrahydrofuran, 3.56 ml, 3.56 mmol) and the reaction allowed to stir at 0° C. for 35 min. Sodium hydroxide (4N, 5.6 ml) and hydrogen peroxide (5.6 ml) were added and the reaction allowed to stir at room temperature for 1 h. Diluted with brine, then extracted three times with dichloromethane. The combined organics were washed twice with brine, dried over sodium sulfate, concentrated in vacuo and purified by column chromatography (50% EtOAc/hexanes). The desired title compound (345 mg) was obtained as a colourless oil as a complex mixture of diastereomers.

Step 3—Ethyl [2-oxo-3-(2-oxobutyl)cyclohexyl]acetate

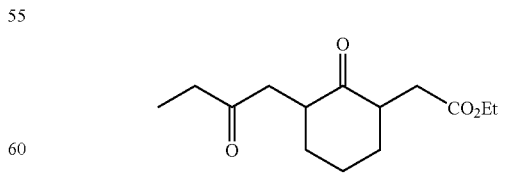

To a stirred solution of ethyl (2-ethyl-7a-hydroxyoctahydro-1-benzofuran-7-yl)acetate (345 mg, 1.34 mmol) in dichloromethane (12 ml) was added pyridine (0.5 ml) and Dess-Martin Periodinane (85.7 mg, 2.02 mmol). After 4 h, the reaction was quenched with a 1:1 mixture of NaHCO$_3$ (sat aq)

and Na$_2$S$_2$O$_3$ (1M, aq.), extracted three times with ethyl acetate, dried over sodium sulfate, concentrated in vacuo, and purified by column chromatography (10-30% EtOAc/hexanes). The desired title compound (211 mg) was obtained as a colourless oil; $^1$H NMR δ (ppm)(CDCl$_3$): 3.63 (2 H, q, J=7.1 Hz), 2.59-2.39 (3 H, m), 2.25 (1 H, dd, J=6.6, 16.5 Hz), 2.10-1.86 (2 H, m), 1.71-1.67 (3 H, m), 1.39-1.29 (2 H, m), 1.14 (1 H, t, J=10.2 Hz), 0.96-0.82 (2 H, m), 0.78-0.68 (3 H, m), 0.56 (3 H, t, J=7.3 Hz).

Step 4—(2-Ethyl-1-{(1R)-1-[4-(trifluoromethyl)phenyl]butyl}-4,5,6,7-tetrahydro-1H-indol-7-yl)acetic acid Using the diketone from the foregoing step and the procedure from example 22, step 2 (employing intermediate 10) followed by the procedure from example 1, step 3 afforded the title compound (9.6 mg) as a mixture of diastereomers, $^1$H NMR δ (ppm)(CDCl$_3$): 7.56-7.51 (2 H, m), 7.14 (1 H, d, J=8.0 Hz), 7.04 (1 H, s), 5.81 (1 H, s), 5.76 (1 H, s), 5.20 (1 H, d, J=7.5 Hz), 3.19 (1 H, d, J=11.8 Hz), 2.53-2.30 (5 H, m), 2.30-2.08 (3 H, m), 1.83 (1 H, s), 1.76 (3 H, s), 1.43-1.29 (3 H, m), 1.20-0.96 (8H, m), 0.90-0.82 (6 H, m).

Example 24

[3-(2,4-dichloroplenyl)-4-(4-fluorophenyl)-1-{1-[4-(trifluoromethyl)phenyl]butyl}-4,5,6,7-tetrahydro-1H-indol-7-yl}acetic acid

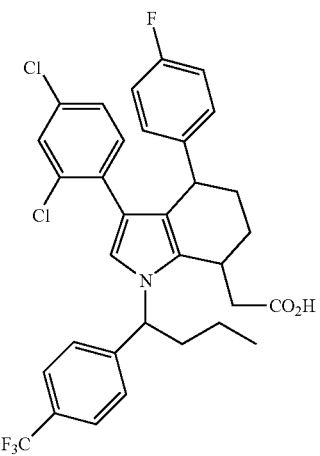

A solution of 2-cyclohexen-1-one (20 g, 0.208 mmol) in tetrahydrofuran (250 ml) was added to a preformed lithium diisopropylamide solution (prepared from diisopropylamine (31 ml) and n-butyllithium (140 ml, 1.6M solution) at −70° C.) over 20 minutes and stirred for a further 20 minutes. Ethyl bromoacetate (25 ml, 0.228 mmol) was added dropwise and the reaction stirred for 1 hour warming to room temperature. The reaction was quenched with 6N HCl (200 ml) and the product extracted into ether (3×300 ml). Combined organic phase washed with saturated sodium chloride, dried over magnesium sulfate and evaporated to dryness. The crude oil was purified by silica chromatography eluting with hexane-ethyl acetate mixtures (10-20%), to give ethyl (2-oxo-cyclohex-3-enyl)acetate as a colourless oil, 11.8 g. 1H NMR δ (ppm) (CDCl$_3$): 6.98-6.94 (1H, m), 6.03-6.00 (1H, m), 4.19-4.11 (2H, m), 2.92-2.82 (2H, m), 2.49-2.41 (2H, m), 2.30-2.23 (1H, m), 2.16-2.11 (1H, m), 1.87-1.77 (1H, m) and 1.28-1.24 (3H, m).

This ester (4 g, 0.022 mmol), copper (I) bromide-dimethyl sulfide complex (4.88 g, 0.023 mmol) in dimethyl sulfide (20 ml) and tetrahydrofuran (120 ml) was cooled to −40° C. under nitrogen and treated dropwise with 4-fluorophenylmagnesium bromide (1M solution in THF, 43.9 ml) so that the temperature did not rise above −40° C. Reaction was stirred for 20 minutes before quenching with 1N HCl (300 ml) and extracting the products with ether (3×300 ml). Combined organic phase washed with saturated sodium chloride, dried over magnesium sulfate and evaporated to dryness. The crude oil was purified by silica chromatography eluting with hexane-ethyl acetate mixtures (10-20%), to give ethyl [4-(4-fluorophenyl)-2-oxo-cyclohexyl]acetate as a colourless oil, 2.8 g. $^1$H NMR δ (ppm) (CDCl$_3$): 7.26-7.11 (2H, m), 7.04-6.94 (2H, m), 4.18-4.11 (2H, m), 3.55-3.44 (1H, m), 3.00-2.90 (1H, m), 2.80-2.73 (2H, m), 2.69-2.55 (1H, m), 2.28-2.17 (2H, m), 2.10-1.88 (2H, m), 1.61-1.42 (1H, m) and 1.31-1.25 (3H, m).

The ester from the foregoing step was transformed to the desired produce using the procedures of Example 1, steps 1-3 with the foregoing ester used in place of ethyl cyclohexaneneacetate in Step 1. Final purification by flash column chromatography (30% EtOAc/hexane) afforded the title compound as a mixture of diastereomers. $^1$H NMR δ (ppm) (CDCl$_3$): 7.67-6.64 (24 H, m), 5.26-5.16 (2 H, m), 4.05-3.88 (2 H, m), 3.51-3.43 (1 H, m), 3.13-3.05 (1 H, m) 2.78-2.73 (4 H, m), 2.43-0.82 (28 H, m).

Example 25

Example 25a ((7R)-3-(2,4-dichlorophenyl)-1-{(1S)-4-methyl-1-[4-(trifluoro methyl)phenyl]pentyl}-4,5,6,7-tetrahydro-1H-indol-7-yl)acetic acid and Example 25b ((7S)-3-(2,4-dichlorophenyl)-1-{(1S)-4-methyl-1-[4-(trifluoro methyl)phenyl]pentyl}-4,5,6,7-tetrahydro-1H-indol-7-yl)acetic acid

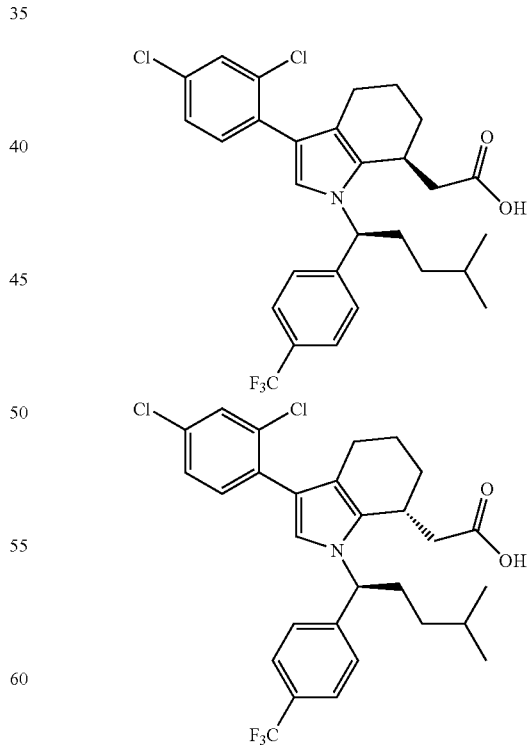

Step 1

To intermediate 21 (0.228 mol) was added Intermediate 19 (30 g, 0.148 mmol) and propionic acid (1.65 ml, 22.2 mmol).

This mixture was heated at 125° C. for 16 h. The mixture was diluted with ethyl acetate, washed twice with 2N HCl and once with water, then dried over sodium sulfate and evaporated to dryness. The crude oil was purified by silica chromatography eluting with (1-5% ethyl acetate/hexanes), to give desired ethyl {3-[1-(2,4-dichlorophenyl)prop-2-en-1-yl]-2-oxocyclohexyl}acetate as a colourless oil (33 g) as a 1.75:1 mixture of diastereomers A and B. $^1$H NMR δ (ppm)(CDCl$_3$): 7.43-7.13 (6 H, m A+B), 6.09-5.99 (1 H, m, A), 5.82-5.72 (1 H, m, B), 5.08-4.96 (4 H, m, A+B), 4.47-4.33 (2 H, m, A+B), 4.14-3.99 (4 H, m, A+B), 3.13-3.01 (2 H, m, A+B), 2.87-2.73 (2 H, m, A+B), 2.58-2.33 (2 H, m, A+B), 2.22-1.88 (6H, m, A+B), 1.77-1.35 (6 H, m, A+B), 1.28-1.20 (8 H, m, A+B). An additional 30 g of product contaminated with ethyl (2-oxocyclohexyl)acetate was obtained.

Step 2

Ethyl {3-[1-(2,4-dichlorophenyl)prop-2-en-1-yl]-2-oxocyclohexyl}acetate (3.5 g, 9.48 mmol) was dissolved in methanol (40 ml) and dichloromethane (80 ml) and cooled to −78° C. Nitrogen and then oxygen were bubbled through the reaction mixture for 5 mins each. Ozone was then bubbled through the reaction mixture until the reaction became a blue colour (1.5 hours). Nitrogen was then bubbled through the reaction for 5 min and dimethylsulfide (7 ml, 94.8 mmol) was added. The reaction was allowed to warm to room temperature and stirred for 16 h, then concentrated in vacuo. After dilution with ethyl acetate, the mixture washed twice with water, dried over sodium sulfate and concentrated in vacuo. The mixture containing the desired diketone and ketals was taken into the next step without further purification.

Step 3

Half of the mixture from the foregoing step (4.74 mmol) was dissolved in toluene (70 ml) and intermediate 8 (1.39 g, 5.69 mmol), acetic acid (0.5 ml) and lithium perchlorate (504 mg, 4.74 mmol) added. A Dean-Stark apparatus was attached and the mixture refluxed for 72 h. After cooling, the reaction was quenched with sodium bicarbonate (sat. aq.) and filtered though Celite™. The aqueous layer was extracted three times with ethyl acetate and the combined organic layers were dried over sodium sulfate and concentrated in vacuo. The residue was purified by column chromatography to give the title compound (1.01 g), a 1:1 mixture of diastereomers A and B, as a pale yellow oil. $^1$H NMR δ (ppm)(CDCl$_3$): 7.60-7.52 (4 H, m, A+B), 7.46 (2 H, d, J=2.0 Hz, A+B), 7.34-7.28 (4 H, m, A+B), 7.24-7.20 (2 H, m, A+B), 7.15 (2H, d, J=8.0 Hz A/B), 7.05 (1 H, s, A), 6.94 (1 H, s, B), 5.18-5.08 (2 H, m, A+B), 4.23-4.07 (4 H, m), 3.41-3.34 (1 H, m, B), 3.04-2.98 (1 H, m, A), 2.59 (2 H, d, J=8.7 Hz A+B), 2.46-2.38 (4 H, m, A+B), 2.27-2.19 (2 H, m, A+B), 2.12-2.04 (6 H, m, A+B), 1.93 (1 H, d, J=15.6 Hz, A/B), 1.80-1.58 (10 H, m A+B), 1.43 (1 H, d, J=6.6 Hz, A/B), 1.34-1.20 (6 H, m, A+B), 0.94-0.86 (12 H, m, A+B); m/z (ES$^+$) 581 (MH$^+$).

Step 4 Hydrolysis was performed by the method of Example 1 Step 3. The residue was purified by column chromatography to give ((7RS)-3-(2,4-dichlorophenyl)-1-{(1S)-4-methyl-1-[4-(trifluoro methyl)phenyl]pentyl}-4,5,6,7-tetrahydro-1H-indol-7-yl)acetic acid (830 mg), as a 1:1 mixture of diastereomers A and B, as a colourless foam. $^1$H NMR δ (ppm)(CDCl$_3$): 7.59 (2 H, d, J=8.2 Hz B), 7.55 (2 H, d, J=8.2 Hz, A), 7.47 (2 H, s, A+B), 7.35-7.28 (4 H, m, A+B), 7.24-7.21 (2 H, m, A+B), 7.13 (2 H, d, J=8.1 Hz), 7.05 (1 H, s), 6.96 (1 H, s), 5.14-5.07 (2 H, m), 3.40-3.36 (1 H, m, B), 3.06-3.01 (1 H, m, A), 2.71-2.63 (2 H, m, A), 2.50-2.34 (4 H, m, A+B), 2.29 (1 H, dd, J=11.0, 15.6 Hz, B), 2.24-2.02 (5 H, m, A+B), 1.88-1.53 (10 H, m, A+B), 1.51-1.41 (1H, d, J=4.6 Hz, A), 1.34-1.12 (3 H, m, A+B), 0.93-0.83 (12 H, m, A+B); m/z (ES$^+$) 550 (M−H$^+$).

The diastereomers could be separated by supercritical fluid chromatography (CHIRALCEL OJ-H 250×10 mm (5μ) column) Column temperature 40° C., Mobile phase: 85/15 CO$_2$/MeOH, Flow rate: 10 mL/min, outlet pressure 100 bar.

Example 25a ((7R)-3-(2,4-dichlorophenyl)-1-{(1S)-4-methyl-1-[4-(trifluoromethyl)phenyl]pentyl}-4,5,6,7-tetrahydro-1H-indol-7-yl)acetic acid eluted at 3.56 min; $^1$H NMR δ (ppm)(CDCl$_3$): 7.59 (2 H, d, J=8.2 Hz), 7.46 (1 H, d, J=2.1 Hz), 7.34-7.29 (3 H, m), 7.23 (1 H, dd, J=8.1, 2.2 Hz), 6.95 (1 H, s), 5.12 (1 H, t, J=7.7 Hz), 3.40-3.35 (1 H, m), 2.48-2.44 (2 H, m), 2.29 (1 H, dd, J=11.0, 15.8 Hz), 2.14-2.08 (2 H, m), 2.05-1.99 (1 H, m), 1.88-1.80 (3 H, m), 1.70-1.50 (2 H, s), 1.25-1.15 (2 H, m), 0.88-0.86 (6 H, m).

Example 25b ((7S)-3-(2,4-dichlorophenyl)-1-{(1S)-4-methyl-1-[4-(trifluoromethyl)phenyl]pentyl}-4,5,6,7-tetrahydro-1H-indol-7-yl)acetic acid eluted at 4.41 min; $^1$H NMR δ (ppm)(CDCl$_3$): 7.55 (2 H, d, J=8.1 Hz), 7.46 (1 H, d, J=2.1 Hz), 7.29 (1 H, d, J=8.4 Hz), 7.22 (2 H, dd, J=8.4, 2.1 Hz), 7.13 (2 H, d, J=8.1 Hz), 7.05 (1 H, s), 5.09 (1 H, dd, J=5.6, 9.6 Hz), 3.07-3.01 (1 H, m), 2.71-2.63 (2 H, m), 2.45-2.42 (2 H, m), 2.25-2.17 (1 H, m), 2.11-2.04 (1 H, m), 1.82-1.77 (2 H, m), 1.73-1.66 (3 H, m), 1.43-1.41 (1 H, m), 1.34-1.24 (1 H, m), 0.93 (3 H, d, J=3.3 Hz), 0.92 (3 H, d, J=3.3 Hz).

Example 26

(3-(2,4-Dichlorophenyl)-1-{3-phenyl-1-[4-(trifluoro methyl)phenyl]propyl}-4,5,6,7-tetrahydro-1H-indol-7-yl)acetic acid

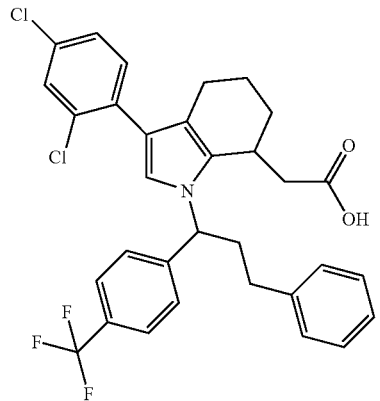

Intermediate 3 (0.2 g, 0.54 mmol) and the product from Example 25, Step 2 (0.18 g, 0.65 mmol) were dissolved in toluene (15 ml). Lithium perchlorate (57 mg, 0.54 mmol) and acetic acid (3 μl, 0.05 mmol) were added and the mixture was refluxed in a Dean Stark apparatus for 2 days. It was then diluted with AcOEt (20 ml), washed with a saturated solution of NaHCO$_3$ (20 ml), dried over MgSO$_4$ and concentrated in vacuo. Purification by chromatography on silica gel eluting with 5% AcOEt/Hexane afforded 30 mg of impure ethyl (3-(2,4-dichlorophenyl)-1-{3-phenyl-1-[4-(trifluoromethyl) phenyl]propyl}-4,5,6,7-tetrahydro-1H-indo 1-7-yl)acetate that was directly used in the next step; m/z (ES$^+$) 614 (MH$^+$).

The ester from the foregoing step (0.03 g, 0.05 mmol) was dissolved in a mixture of dioxane (7 ml)/water (2 ml). Then LiOH (12 mg, 0.5 mmol) was added and the solution heated

Example 27

(1-{4,4-Dimethyl-1-[4-(trifluoromethyl)phenyl]pentyl}-2-isopropyl-4,5,6,7-tetrahydro-1H-indol-7-yl)acetic acid

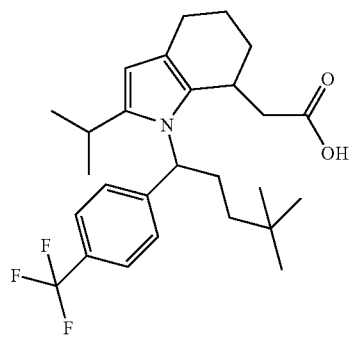

Ethyl [3-(3-methyl-2-oxobutyl)-2-oxocyclohexyl]acetate (0.25 g, 0.93 mmol) (prepared using the procedure of example 25 step 1 [using intermediate 16 in place of Intermediate 19] followed by the procedure used in the preparation of intermediate 13) and intermediate 5 (0.29 g, 1.1 mmol) were dissolved in toluene (25 ml). Lithium perchlorate (99 mg, 0.93 mmol) and acetic acid (5 µl, 0.09 mmol) were added and the mixture was refluxed in a Dean Stark apparatus for 12 hours. It was then diluted with AcOEt (20 ml), washed with a saturated solution of NaHCO$_3$ (20 ml), dried over MgSO$_4$ and concentrated in vacuo. Purification by chromatography on silica gel eluting with 5% AcOEt/Hexane afforded 40 mg of impure ethyl(1-{4,4-dimethyl-1-[4-(trifluoromethyl)phenyl]pentyl}-2-isopropyl-4,5,6,7-tetrahydro-1H-indol-7-yl)acetate that was directly used in the next step; m/z (ES$^+$) 492 (MH$^+$).

Impure ester from the foregoing step (40 mg, 0.08 mmol) was dissolved in a mixture of THF (5 ml)/water (1 ml) then LiOH (20 mg, 0.8 mmol) was added and the solution heated to 60° C. for 14 h. The reaction mixture was then diluted with AcOEt (20 ml), washed with 2.0N HCl (20 ml), brine (20 ml), dried over Na$_2$SO$_4$ and concentrated in vacuo. The residue was purified by chromatography on silica gel eluting with 25% AcOEt/Hexane to afford 14 mg of the title compound as a 1:1.4 mixture of diastereoisomers; m/z (ES$^+$) 464 (MH$^+$); m/z (ES$^-$) 462 (M−H$^+$).

Example 28

(2-Isopropyl-1-{3-phenyl-1-[4-(trifluoromethyl)phenyl]propyl}-4,5,6,7-tetrahydro-1H-indol-7-yl)acetic acid

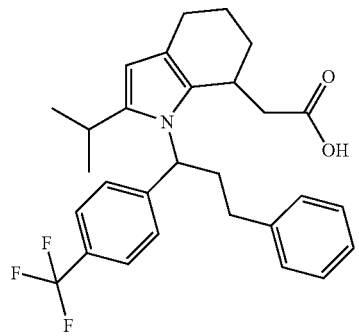

Prepared by analogy to Example 27 using intermediate 3 in place of intermediate 5; m/z (ES$^+$) 484 (MH$^+$); m/z (ES$^-$) 482 (M−H$^+$).

Example 29

(2-Isopropyl-1-{(1S)-4-methyl-1-[4-(trifluoromethyl)phenyl]pentyl}-4,5,6,7-tetrahydro-1H-indol-7-yl)acetic acid

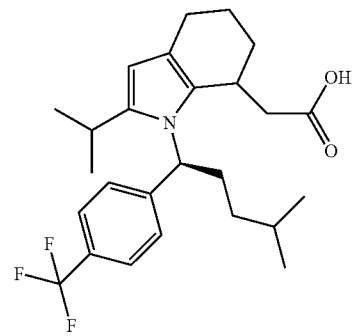

Prepared by analogy to Example 27 using intermediate 8 in place of intermediate 5; m/z (ES$^-$) 448 (M−H$^+$). Diastereomers were separated by SFC by analogy to Example 25.

Example 30

2-Isopropyl-1-{(1S)-4-methyl-1-[4-(trifluoromethyl)phenyl]pentyl}-7-(1H-tetrazol-5-ylmethyl)-4,5,6,7-tetrahydro-1H-indole

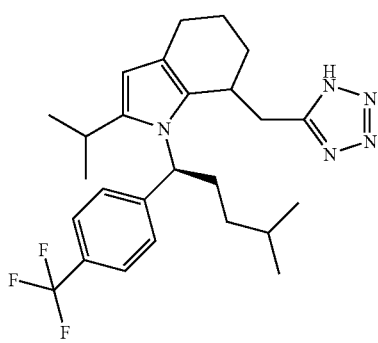

The product from Example 29 (0.35 g, 0.78 mmol) was dissolved in dioxane (10 ml). $NH_3$ 0.5M in dioxane (1.87 ml, 0.93 mmol) was added followed by HOBT (158 mg, 1.2 mmol), EDC.HCl (224 mg, 1.2 mmol) and DIEA (0.35 ml, 1.95 mmol). The mixture was stirred at RT for 14 hours. It was then diluted with dichloromethane (30 ml), washed with water (20 ml), brine (20 ml) and concentrated under reduced pressure. Purification by chromatography on silica gel eluting with a gradient 20-25% AcOEt/Hexane afforded the desired amide (350 mg, quantitative yield) as a colourless solid (m/z (ES$^+$) 449 (MH$^+$)) which was dissolved in dichloromethane (10 ml) and Burgess reagent (0.37 g, 1.5 mmol) added. The mixture was stirred at RT for 14 hours and after evaporation of the solvent under reduced pressure the residue was purified by chromatography on silica gel eluting with 10% AcOEt/Hexane to afford the desired nitrile (250 mg, 74%) as a colourless oil (m/z (ES$^+$) 431 (MH$^+$)) which was dissolved in DMF (10 ml). $NaN_3$ (378 mg, 0.58 mmol) and $NH_4Cl$ (310 mg, 0.58 mmol) were added and the mixture was heated to 125° C. for 14 hours. It was then diluted with AcOEt (30 ml), washed with 0.1N HCl (10 ml), brine (10 ml), dried over $MgSO_4$ and concentrated. Purification by chromatography on silica gel eluting with 20% AcOEt/Hexane afforded the desired tetrazole as a 1:1 mixture of diastereoisomers (7 mg, 3%); $^1$H NMR δ (ppm)(CDCl$_3$, 360 MHz): 7.54-7.49 (4 H, m, A+B), 7.26-7.22 (2H, m, A+B), 7.14-7.12 (2 H, m, A+B), 5.87 (1 H, s, A/B), 5.84 (1 H, s, A/B), 5.38-5.36 (1 H, m, A/B), 5.32-5.28 (1 H, m, A/B), 3.42-3.30 (2 H, m, A+B), 3.21-2.92 (4 H, m, A+B), 2.58-2.45 (4 H, m, A+B), 1.74-1.49 (6 H, m, A+B), 1.46-1.33 (2 H, m, A+B), 1.24-1.20 (6 H, m A+B), 1.15-1.09 (6 H, m, A+B), 0.95-0.86 (12 H, m, A+B); m/z (ES$^+$) 474 (MH$^+$); m/z (ES$^-$) 472 (M–H$^+$).

Example 31

(1-{[4-(trifluoromethyl)phenyl]methyl}-2-isopropyl-4,5,6,7-tetrahydro-1H-indol-7-yl)acetic acid

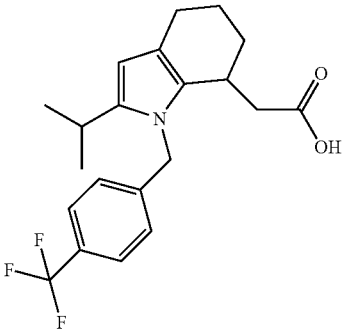

Prepared by analogy to Example 27 using 4-(trifluoromethyl)benzylamine in place of intermediate 5; m/z (ES$^-$) 378 (M–H$^+$).

Example 32

(1-{[4-(Trifluoromethyl)phenyl]methyl}-2-tert-butyl-4,5,6,7-tetrahydro-1H-indol-7-yl)acetic acid

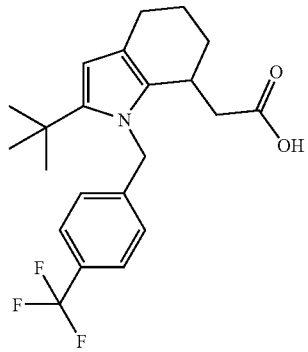

Prepared by analogy to Example 19 using 1-bromo-3,3-dimethylhexan-2-one in place of 2-bromo-1-phenylethanone in step 1 and 4-(trifluoromethyl)benzylamine in place of intermediate 1 in step 2; m/z (ES$^-$) 392 (M–H$^+$).

Example 33

2-Isopropyl-1-{(1S)-4-methyl 1-[4-(trifluoromethyl)phenyl]pentyl}-1,4,5,6-tetrahydrocyclopenta[b]pyrrol-6-yl)acetic acid

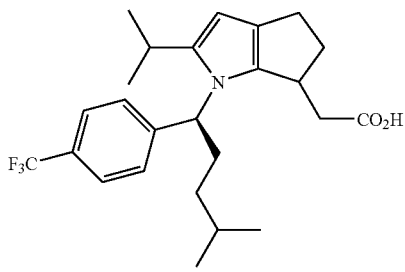

Ethyl (2-pyrrolidin-1-ylcyclopent-2-en-1-yl)acetate was prepared from 2-cyclopentanone acetate using the procedure used to prepare intermediate 2 and was alkylated with prenyl bromide using the procedure of example 19, step 1 to afford ethyl [3-(3-methylbut-2-en-1-yl)-2-oxocyclopentyl]acetate as a mixture of diastereomers; $^1$H NMR δ (ppm)(CDCl$_3$): 5.10-5.04 (1 H, m), 4.17-4.07 (2 H, m), 2.84-2.51 (2 H, m), 2.48-2.14 (4 H, m), 2.12-2.06 (1 H, m), 2.02-1.88 (1 H, m), 1.73-1.61 (7 H, m), 1.55-1.45 (1 H, m), 1.28-1.22 (3 H, m).

This mixture (4.0 g, 15.87 mmol) was dissolved in dichloromethane (50 ml) and cooled to 0° C. m-CPBA (70%, 4.28 g, 17.46 mmol) was added carefully, and the mixture then stirred for 1 h. The reaction was quenched with 1N NaOH and extracted three times with ethyl acetate and then the combined organics washed with 1N NaOH and brine. The organics were dried over sodium sulfate, concentrated and the crude ethyl {3-[(3,3-dimethyloxiran-2-yl)methyl]-2-oxocyclopentyl}acetate purified (20% ethyl acetate/hexanes) by a very quick silica plug column and used directly in the next reaction.

The foregoing product (4.28 g, 15.87 mmol) was dissolved in toluene (70 ml) and lithium perchlorate added (1.68 g, 15.87 mmol). The reaction was heated to reflux and stirred for 2 h. After cooling, the reaction was quenched with saturated aqueous sodium bicarbonate, extracted three times with ethyl acetate, dried over sodium sulfate and concentrated. The crude product was purified by column chromatography (5-10% ethyl acetate/hexanes) to afford the desired ethyl [3-(3-methyl-2-oxobutyl)-2-oxocyclopentyl]acetate (3.6 g) as a colourless oil; $^1$H NMR δ (ppm)(CDCl$_3$): 4.16-4.10 (2 H, m), 3.08-2.82 (2 H, m), 2.77-2.71 (1 H, m), 2.69-2.59 (1 H, m), 2.55-2.37 (1 H, m), 2.25-2.07 (2 H, m), 2.01-1.71 (2 H, m), 1.43-1.31 (1 H, m), 1.28-1.22 (2 H, m), 1.19 (2 H, d, J 9.6 Hz), 1.13-1.09 (6 H, m).

This ethyl [3-(3-methyl-2-oxobutyl)-2-oxocyclopentyl]acetate was transformed to the desired 2-isopropyl-1-{(1S)-4-methyl-1-[4-(trifluoromethyl)phenyl]pentyl}-1,4,5,6-tetrahydrocyclopenta[b]pyrrol-6-yl)acetic acid using the procedures from Example 25, steps 3 and 4; m/z (ES$^-$) 434 (M−H$^+$).

Example 34

(2-[4-(trifluoromethyl)phenyl]-1-{(1S)-4-methyl-1-[4-(trifluoromethyl)phenyl]pentyl}-4,5,6,7-tetrahydro-1H-indol-7-yl)acetic acid

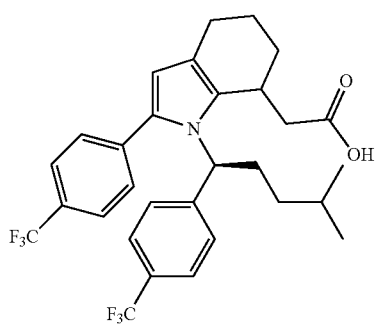

Prepared using the procedures from Example 25, steps 1-4. In step 1, intermediate 18 was used in the place of Intermediate 19; m/z (ES$^-$) 550 (M−H$^+$). Diastereomers were separated by SFC by analogy to Example 25.

Example 35

(2-Methyl-1-{(1R)-1-[4-(trifluoromethyl)phenyl]butyl}-4,5,6,7-tetrahydro-1H-indol-7-yl)acetic acid

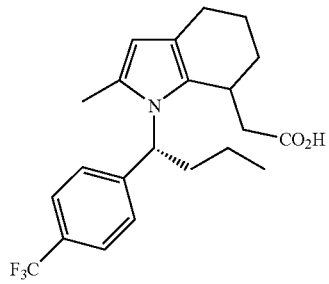

Prepared using procedures from Example 22 using intermediate 10 in place of intermediate 1 in step 2; m/z (ES$^-$) 392 (M−H$^+$).

Example 36

(2-Isopropyl-1-{(1R)-4-methyl-1-[4-(trifluoromethyl)phenyl]pentyl}-4,5,6,7-tetrahydro-1H-indol-7-yl)acetic acid

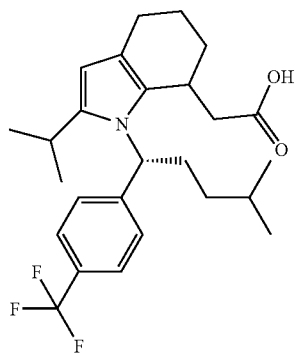

Prepared using the procedure of example 25 step 1-4 using intermediate 16 in place of Intermediate 19 in step 1, and the procedure used in the preparation of intermediate 13 instead of example 25 step 2. In step 3, ent-intermediate 8 was used in place of intermediate 8; m/z (ES$^-$) 448 (M−H$^+$). Diastereomers were separated by SFC by analogy to Example 25.

Example 37

(2-Isopropyl-1-{(is)-1-[4-(trifluoromethyl)phenyl]butyl}-4,5,6,7-tetrahydro-1H-indol-7-yl)acetic acid

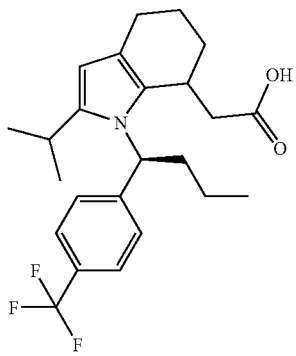

Prepared using the procedure of example 25 step 1-4 using intermediate 16 in place of Intermediate 19 in step 1, and the procedure used in the preparation of intermediate 13 instead of example 25 step 2. In step 3, intermediate 9 was used in place of intermediate 8; m/z (ES⁻) 420 (M−H⁺). Diastereomers were separated by SFC by analogy to Example 25.

Example 38

(6-ethyl-2-isopropyl-1-{(1S)-4-methyl-1-[4-(trifluoromethyl)phenyl]pentyl}-4,5,6,7-tetrahydro-1H-indol-7-yl)acetic acid

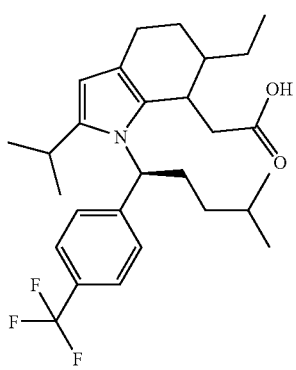

Prepared using the procedures from Example 25, steps 1-4 using intermediate 16 in place of Intermediate 19 in step 1, and the procedure used in the preparation of intermediate 13 instead of example 25 step 2. Also in step 1, a mixture of ethyl [(1R,6S)-2-ethoxy-6-ethylcyclohex-2-en-1-yl]acetate and ethyl [(1R,6S)-2,2-diethoxy-6-ethylcyclohexyl]acetate [prepared from intermediate 14 and the procedure used for the preparation of intermediate 21], was used in place of intermediate 21; m/z (ES⁻) 476 (M−H⁺). Diastereomers were separated by SFC by analogy to Example 25.

Example 39

(2-Isopropyl-1-{(1R)-1-[4-(trifluoromethyl)phenyl]butyl}-4,5,6,7-tetrahydro-1H-indol-7-yl)acetic acid

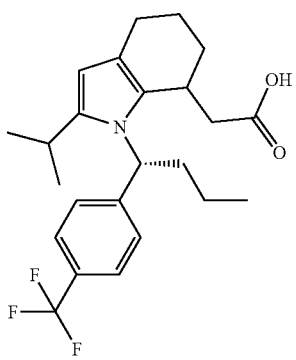

Prepared using the procedure of example 25 step 1-4 using intermediate 16 in place of Intermediate 19 in step 1, and the procedure used in the preparation of intermediate 13 instead of example 25 step 2. In step 3, intermediate 10 was used in place of intermediate 8; m/z (ES⁻) 420 (M−H⁺).

Example 40

(2-Cyclohexyl-1-{(1S)-4-methyl-1-[4-(trifluoromethyl)phenyl]pentyl}-4,5,6,7-tetrahydro-1H-indol-7-yl)acetic acid

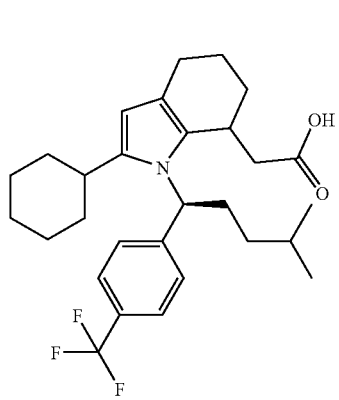

Prepared using the procedures from Example 25, steps 1-4 (using intermediate 17 in the place of Intermediate 19 in step 1); m/z (ES⁻) 488 (M−H⁺). Diastereomers were separated by SFC by analogy to Example 25.

Example 41

(2-Isopropyl-1-{(1S)-4-methyl-1-[4-(trifluoromethyl)phenyl]pentyl}-4,5,6,7-tetrahydro-1H-indol-7-yl)acetic acid

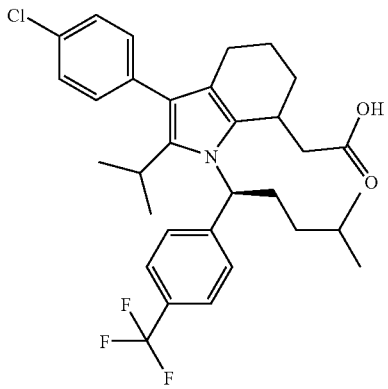

Prepared using the procedures from Example 25, steps 1 and 2 (using intermediate 20 in the place of Intermediate 19 in step 1) followed by the procedure from example 21, step 2 and finally the procedure from example 1, step 3; m/z (ES⁻) 558 (M−H⁺). Diastereomers were separated by mass directed HPLC (Agilent System) by analogy to Example 25.

Example 42

(2-Isopropyl-1-{(1S)-4-methyl-1-[4-(trifluoromethyl)phenyl]pentyl}-4,5,6,7-tetrahydro-1H-indol-7-yl)acetic acid

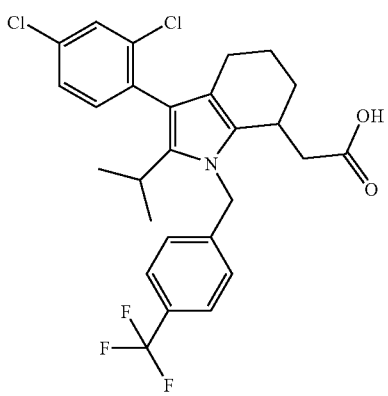

Prepared using the procedures from Example 25, steps 1-4. (2E)-3-(2,4-dichlorophenyl)-2-isopropylprop-2-en-1-ol [prepared by analogy to intermediate 20] was used in the place of Intermediate 19 in step 1) and 4-(trifluoromethyl)benzylamine was used in the place of intermediate 8 in step 3; m/z (ES⁻) 522 (M−H⁺).

Example 43

(3-(2,4-dichlorophenyl)-1-{(1R)-4-methyl-1-[4-(trifluoromethyl)phenyl]pentyl}-4,5,6,7-tetrahydro-1H-indol-7-yl)acetic

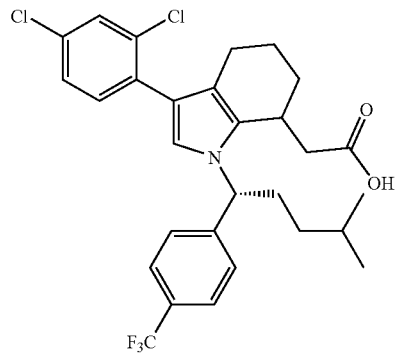

Prepared using the procedures from Example 25, steps 1-4 using ent-intermediate 8 in place of intermediate 8 in step 3; m/z (ES⁻) 550 (M−H⁺). Diastereomers were separated by SFC by analogy to Example 25.

Example 44

(3-(2,4-dichlorophenyl)-1-{(1R)-1-[4-(trifluoromethyl)phenyl]pentyl}-4,5,6,7-tetra hydro-1H-indol-7-yl)acetic acid

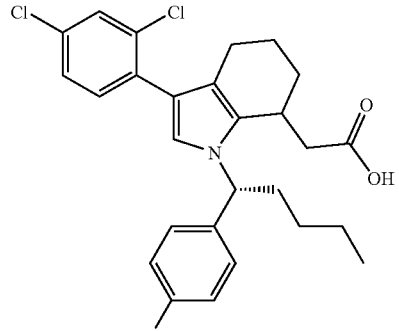

Prepared using the procedures from Example 25, steps 1-4 using intermediate 11 in place of intermediate 8 in step 3; m/z (ES⁻) 536 (M−H⁺). Diastereomers were separated by SFC by analogy to Example 25.

Example 45

3-phenyl-1-{(1S)-4-methyl-1-[4-(trifluoromethyl)phenyl]pentyl}-4,5,6,7-tetra hydro-1H-indol-7-yl)acetic acid

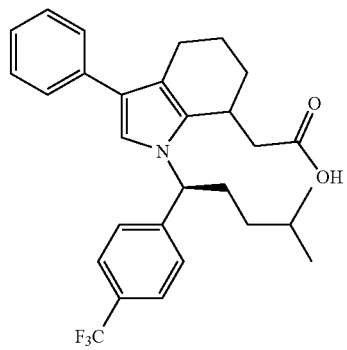

Prepared using the procedures from Example 25, steps 1-4 using cinnamyl alcohol in the place of Intermediate 19 in step 1; m/z (ES⁻) 482 (M–H⁺). Diastereomers were separated by SFC by analogy to Example 25.

Example 46

{3-(2,4-dichlorophenyl)-1-[4-(trifluoromethyl)benzyl]-4,5,6,7-tetrahydro-1H-indol-7-yl}acetic acid

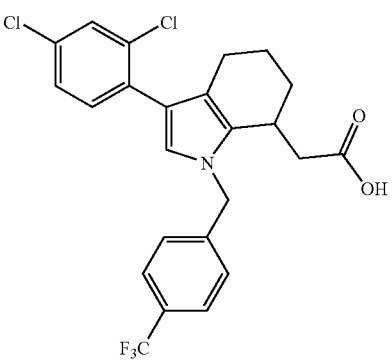

Prepared using the procedures from Example 25, steps 1-4 using 4-(trifluoromethyl)benzylamine in place of intermediate 8 in step 3; m/z (ES⁻) 480 (M–H⁺).

Example 47

{3-(2-methyl-2-propyl)-1-[4-(trifluoromethyl)benzyl]-4,5,6,7-tetrahydro-1H-indol-7-yl}acetic acid

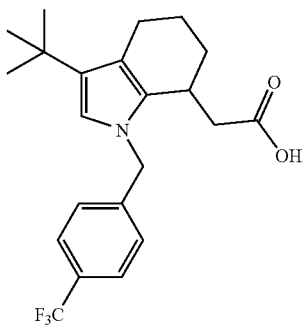

Prepared using the procedures from Example 25, steps 1-4 using intermediate 15 in place of Intermediate 19 in step 1 and 4-(trifluoromethyl)benzylamine in place of intermediate 8 in step 3; m/z (ES⁻) 392 (M–H⁺).

Example 48

(3-(2-methyl-2-propyl)-1-{(1R)-4-methyl-1-[4-(trifluoromethyl)phenyl]pentyl}-4,5,6,7-tetrahydro-1H-indol-7-yl)acetic acid

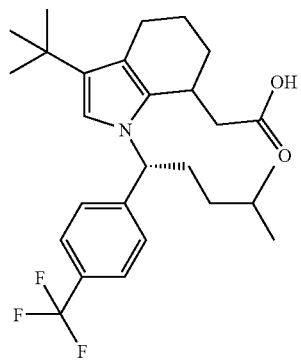

Prepared using the procedures from Example 25, steps 1 and 2 (using intermediate 15 in place of Intermediate 19 in step 1) followed by the procedure from example 21, step 2 (using ent-intermediate 8 in place of intermediate 8) and finally the procedure from example 1, step 3; m/z (ES⁻) 462 (M–H⁺). Diastereomers were separated by SFC by analogy to Example 25.

Examples 49-66

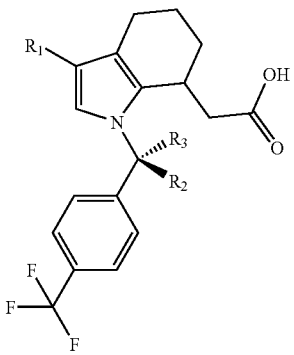

Examples 49-66 were prepared following the procedures of Examples 1 or 2. In step 1, intermediate 9, 10, 22 or ent-intermediate 8 was used as appropriate. In step 2, the appropriate nitroalkene was used:—when not available commercially, the nitroalkenes were prepared by published methods, e.g. base-catalysed condensation of $R^1$CHO with nitromethane. The products were generally isolated as a mixture of two diastereomers which could be separated using SFC or mass-directed HPLC methods analogously to those described previously.

| Ex. No. | $R_1$ | $R_2$ | $R_3$ | m/z (ES⁻) (M – H⁺) |
|---|---|---|---|---|
| 49 | 2-nitrophenyl | H | n-propyl | 499 |
| 50 | 4-tert-butylphenyl | H | n-propyl | 510 |
| 51 | 2,5-dimethylphenyl | H | n-propyl | 482 |
| 52 | 4-chloro-2-fluorophenyl | H | 4-methylbutyl | 534 |
| 53 | 2,4-bis(CF₃)phenyl | H | n-propyl | 590 |
| 54 | 4-cyanophenyl | H | n-propyl | 481 |
| 55 | 2,5-bis(CF₃)phenyl | n-propyl | H | 590 |
| 56 | 2,4-difluorophenyl | H | 4-methylbutyl | 518 |
| 57 | 2,4,6-trichlorophenyl | H | n-propyl | 556 |
| 58 | 2,5-bis(CF₃)phenyl | H | 4-methylbutyl | 618 |
| 59 | 4-(CF₃O)phenyl | H | n-propyl | 538 |
| 60 | 2,5-dichlorophenyl | H | 4-methylbutyl | 550 |
| 61 | 4-(CF₃)phenyl | H | n-propyl | 522 |
| 62 | 2,4-dimethylphenyl | H | n-propyl | 482 |
| 63 | 2,4-dichlorophenyl | H | 3-methylpropyl | 536 |
| 64 | 2,4-dimethoxyphenyl | H | n-propyl | 514 |
| 65 | 2,5-bis(CF₃)phenyl | H | n-propyl | 590 |
| 66 | 4-methylnaphth-1-yl | H | n-propyl | 520 |

Example 67

(3-[2-methyl-4-chlorophenyl]-1-{1-[4-(trifluoromethyl)phenyl]butyl}-4,5,6,7-tetrahydro-1H-indol-7-yl)acetic acid

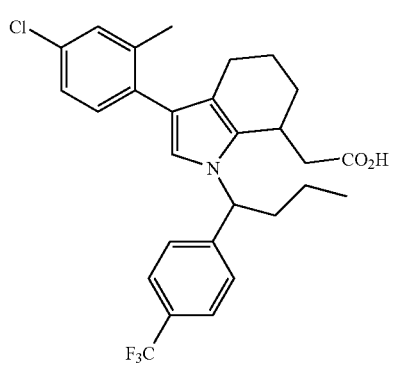

Prepared by analogy to example 17 using methylboronic acid in place of n-butylboronic acid; m/z (ES⁻) 502 (M–H⁺).

Example 68

(3-[2-phenyl-4-chlorophenyl]-1-{1-[4-(trifluoromethyl)phenyl]butyl}-4,5,6,7-tetrahydro-1H-indol-7-yl)acetic acid

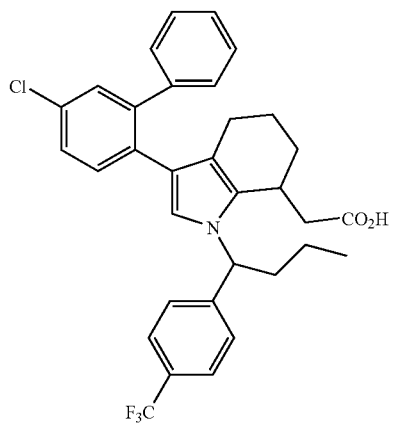

Prepared by analogy to example 17 using phenylboronic acid in place of n-butylboronic acid; m/z (ES⁻) 564 (M–H⁺).

Example 69

(3-(2,4-dichlorophenyl)-1-{1-[4-(trifluoromethyl)phenyl]butyl}-1,4,5,6-tetrahydrocyclopenta[b]pyrrol-6-yl)acetic acid

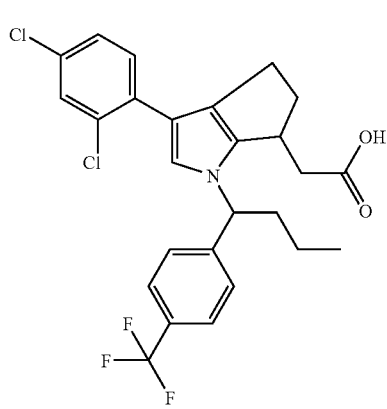

Prepared following the procedures of Example 2. In step 1, 2-cyclopentanone acetate was used in place of cyclohexanone acetate. m/z (ES⁻) 508 (M−H⁺).

Example 70

(3-(2,4-dichlorophenyl)-1-{(1R)-1-[4-(trifluoromethyl)phenyl]butyl}-1,4,5,6,7,8-hexahydrocyclohepta[b]pyrrol-8-yl)acetic acid

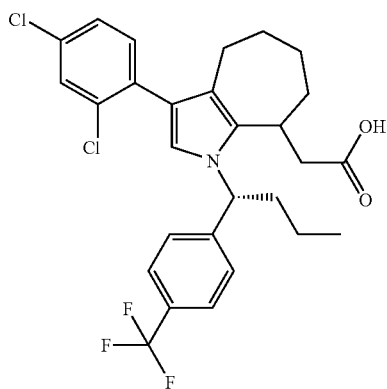

Prepared following the procedures of Example 2. In step 1, 2-cycloheptanone acetate was used in place of cyclohexanone acetate and intermediate 10 was used in place of intermediate 1. m/z (ES⁻) 536 (M−H⁺).

Example 71

(3-(2,4-Dichlorophenyl)-1-{1-[2,5-bis(trifluoromethyl)phenyl]butyl}-4,5,6,7-tetrahydro-1H-indol-7-yl)acetic acid

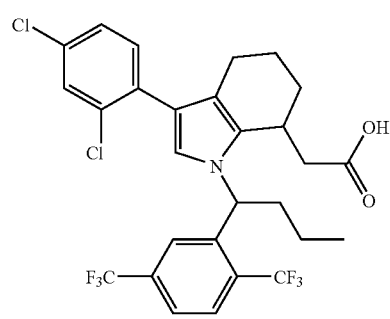

Prepared following the procedures of Example 2. In step 1, intermediate 7 was used in place of intermediate 1. m/z (ES⁻) 590 (M−H⁺).

Example 72

(3-(2,4-Dichlorophenyl)-1-{1-[2,4-bis(trifluoromethyl)phenyl]butyl}-4,5,6,7-tetrahydro-1H-indol-7-yl)acetic acid

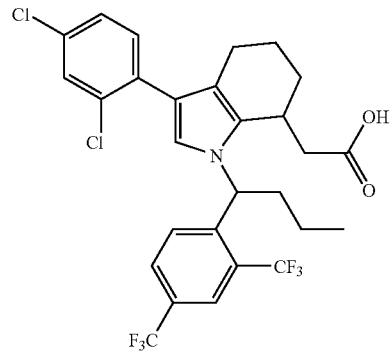

Prepared following the procedures of Example 2. In step 1, intermediate 6 was used in place of intermediate 1. m/z (ES⁻) 590 (M−H⁺).

Example 73

((6S)-3-(2,4-dichlorophenyl)-6-ethyl-1-{(1R)-1-[4-(trifluoromethyl)phenyl]butyl}-4,5,6,7-tetrahydro-1H-indol-7-yl)acetic acid

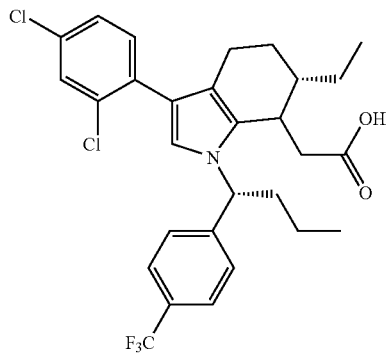

Prepared following the procedures of Example 2. In step 1, intermediate 14 was used in place of 2-cyclohexanone acetate and intermediate 10 was used in place of intermediate 1. m/z (ES$^-$) 550 (M–H$^+$).

Example 74

((6S)-3-(4-chlorophenyl)-6-ethyl-1-{(1R)-1-[4-(trifluoromethyl)phenyl]butyl}-4,5,6,7-tetrahydro-1H-indol-7-yl)acetic acid

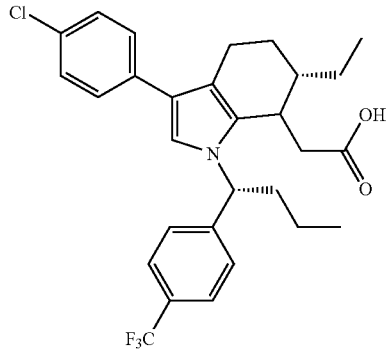

Prepared following the procedures of Example 2. In step 1, intermediate 14 was used in place of 2-cyclohexanone acetate and intermediate 10 was used in place of intermediate 1. In step 2, 2-(4-chlorophenyl)-1-nitroethene was used in place of 2-(2,4-dichlorophenyl)-1-nitroethene. m/z (ES$^-$) 516 (M–H$^+$).

Example 75

((6S)-3-(2,4-dichlorophenyl)-6-ethyl-1-{(1R)-4-methyl-1-[4-(trifluoromethyl)phenyl]pentyl}-4,5,6,7-tetrahydro-1H-indol-7-yl)acetic acid

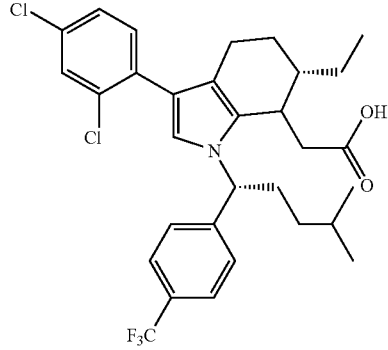

Prepared following the procedures of Example 2. In step 1, intermediate 14 was used in place of 2-cyclohexanone acetate and ent-intermediate 8 was used in place of intermediate 1. m/z (ES$^-$) 578 (M–H$^+$).

Example 76

(3-(2,4-dichlorophenyl)-1-{1-[4-(trifluoromethyl)phenyl]butyl}-4,5,6,7-tetrahydro-1H-indazol-7-yl)acetic acid

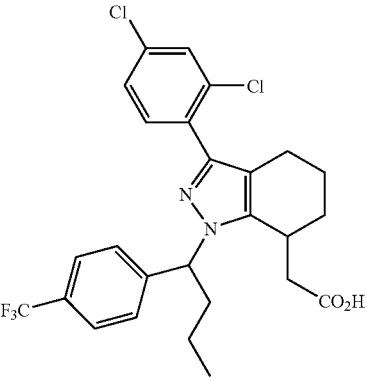

Intermediate 2 (2 g, 8.44 mmol) was dissolved in dioxane (50 ml) and triethylamine (1.18 ml, 8.44 mmol) and 2,4-dichlorobenzoyl chloride (1.76 g, 844 mmol) added. The reaction mixture was stirred at reflux for 16 h. The mixture was then allowed to cool and diluted with ethyl acetate and washed with saturated sodium bicarbonate and then brine. The organics were dried over sodium sulfate and purified by column chromatography to give the desired ethyl [3-(2,4-dichlorobenzoyl)-2-oxocyclohexyl]acetate (220 mg) as a colourless oil. $^1$H NMR δ (ppm)(CDCl$_3$): 7.36 (1H, d, J=2.0 Hz), 7.23, (1 H, dd, J=8.3, 2.0 Hz), 7.12 (1 H, d, J=8.3 Hz), 4.13-4.07 (2 H, m), 2.93-2.84 (1 H, m), 2.78 (1 H, dd, J=16.1, 5.9 Hz), 2.45 (1 H, dd, J=16.1, 8.3 Hz), 2.11-1.84 (4 H, m), 1.70-1.62 (1 H, m), 1.51-1.40 (2 H, m), 1.20 (3 H, t, J=7.0 Hz).

The diketone from the foregoing step (50 mg, 0.14 mmol) and the HCl salt of intermediate 23 (200 mg) were dissolved in NMP and heated in a Smith microwave reactor for 50 min at 220° C. The mixture was then diluted with ethyl acetate and water. The layers were separated and the aqueous layer was extracted with further ethyl acetate. The combined organics were dried (sodium sulfate) and concentrated and then taken back up in diethyl ether. 1N HCl in ether was added and the reaction mixture filtered. The filtrate was concentrated and taken up in DMSO and purified by mass directed HPLC to afford the desired pyrazole; m/z (ES+) 553 (M+H+) which was hydrolysed using the procedure of Example 1 Step 3 to give the desired product; m/z (ES−) 523 (M−H+).

The invention claimed is:

1. A compound of formula I:

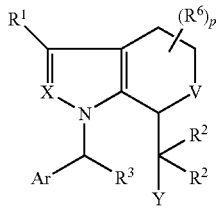

wherein V represents a bond, $CH_2$ or $CH_2CH_2$;

X represents $CR^{1a}$ or N;

Y represents $CO_2H$ or tetrazole;

Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$, $OR^4$, $S(O)_tR^4$ where t is 0, 1 or 2, $CO_2R^4$, tetrazole, $N(R^4)_2$, $NHCOR^5$, $NHCON(R^4)_2$, $CON(R^4)_2$, $SO_2N(R^4)_2$, $NHSO_2R^5$, $COR^5$, or $OCOR^5$;

$R^1$ represents H or a nonaromatic hydrocarbon group of up to 10 carbon atoms optionally substituted with up to 3 halogen substituents or with CN, $CF_3$, $OR^4$, $S(O)_tR^4$ where t is 0, 1 or 2, $CO_2R^4$, $CON(R^4)_2$, $SO_2N(R^4)_2$, $COR^4$, $OCOR^5$ or $NR^4COR^5$;

or $R^1$ represents phenyl, naphthyl, benzyl or heteroaryl any of which optionally bears up to 3 substituents selected from halogen, $CF_3$, $OCF_3$, CN, $NO_2$ $R^5$, $OR^4$, $CO_2R^4$, $S(O)_tR^4$ where t is 0, 1 or 2, $CON(R^4)_2$, $SO_2N(R^4)_2$, $COR^4$, $OCOR^5$ or $NR^4COR^5$;

$R^{1a}$ has the same definition as $R^1$;

each $R^2$ is independently H or $C_{1-4}$alkyl;

$R^3$ is H or a hydrocarbon group containing up to 10 carbon atoms which is optionally substituted with halogen, $CF_3$, $C_{1-4}$alkoxy or $C_{1-4}$alkylthio;

$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl; or two $R^4$ groups attached to the same nitrogen atom may complete a 5- or 6-membered heterocyclic ring;

$R^5$ represents $R^4$ that is other than H;

p is 0, 1 or 2; and $R^6$ represents $C_{1-6}$alkyl, $C_{2-6}$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;

or a pharmaceutically acceptable salt thereof.

2. A compound according to claim 1 of formula II:

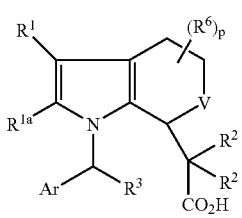

or a pharmaceutically acceptable salt thereof;
wherein V, Ar, p, $R^1$, $R^{1a}$, $R^2$, $R^3$ and $R^6$ are as defined in claim 1.

3. A compound according to claim 1 of formula III:

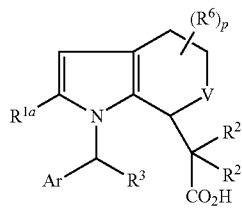

or a pharmaceutically acceptable salt thereof;
wherein V, Ar, p, $R^{1a}$, $R^2$, $R^3$ and $R^6$ are as defined in claim 1.

4. A compound according to claim 2 wherein $R^1$ is selected from H, hydrocarbon of up to 6 carbon atoms and phenyl which optionally bears up to 3 substituents selected from halogen, $C_{1-6}$alkyl, $OCF_3$, methoxy and $CF_3$.

5. A compound according to claim 3 wherein $R^{1a}$ is selected from $C_{1-6}$alkyl, $C_{3-7}$cycloalkyl and phenyl which optionally bears up to 3 substituents selected from halogen, $C_{1-6}$alkyl, $OCF_3$, methoxy and $CF_3$.

6. A compound according to claim 1 in which V represents $CH_2$ and each $R^2$ is H.

7. A compound according to claim 1 in which $R^3$ is an alkyl group of 2 to 6 carbon atoms.

8. A compound according to claim 1 in which Ar is 4-trifluoromethylphenyl.

9. A pharmaceutical composition comprising a compound according to claim 1 and a pharmaceutically acceptable carrier.

10. A method of treating Alzheimer's disease comprising administering to a patient in need thereof a therapeutically effective amount of a compound according to claim 1.

11. A process for preparing a compound of formula I as defined in claim 1 in which X represents $CR^{1a}$, comprising reaction of an amine of formula:

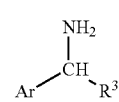

with a 1,4-dicarbonyl compound of formula:

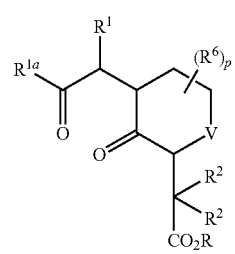

followed by hydrolysis,
wherein R represents methyl or ethyl and all other variables are as defined in claim 1.

* * * * *